(12) United States Patent
Ben-Tsur et al.

(10) Patent No.: US 12,083,303 B2
(45) Date of Patent: Sep. 10, 2024

(54) DEVICE AND METHOD FOR DELIVERING A FLOWABLE INGESTIBLE MEDICAMENT INTO THE GASTROINTESTINAL TRACT OF A USER

(71) Applicant: VIBRANT LTD., Yokneam (IL)

(72) Inventors: Lior Ben-Tsur, Netanya (IL); Ronny Shabat, Kibbutz Yizra'el (IL); Shai Molnar, Shorashim (IL)

(73) Assignee: Vibrant Ltd., Yokneam (IL)

( * ) Notice: Subject to any disclaimer, the term of this patent is extended or adjusted under 35 U.S.C. 154(b) by 738 days.

(21) Appl. No.: 17/246,643

(22) Filed: May 2, 2021

(65) Prior Publication Data

US 2021/0322741 A1 Oct. 21, 2021

Related U.S. Application Data

(63) Continuation-in-part of application No. PCT/IB2020/050433, filed on Jan. 21, 2020, and a
(Continued)

(30) Foreign Application Priority Data

Jan. 21, 2019 (GB) ..................... 1900780

(51) Int. Cl.
*A61M 31/00* (2006.01)
*A61M 39/22* (2006.01)
(52) U.S. Cl.
CPC .......... *A61M 31/002* (2013.01); *A61M 39/22* (2013.01); *A61M 2039/226* (2013.01);
(Continued)
(58) Field of Classification Search
CPC ........ A61M 31/002; A61M 2210/1042; A61M 31/00
See application file for complete search history.

(56) References Cited

U.S. PATENT DOCUMENTS 3,485,235 A 12/1969 Felson
4,239,040 A 12/1980 Hosoya et al.
(Continued)

FOREIGN PATENT DOCUMENTS

CN 1829466 A 9/2006
CN 101810481 A 8/2010
(Continued)

OTHER PUBLICATIONS

Machine Translation (by Google Patents) for CN 101810481 published on Aug. 25, 2010.
(Continued)

*Primary Examiner* — William R Carpenter
(74) *Attorney, Agent, or Firm* — Momentum IP; Marc Van Dyke

(57) ABSTRACT

A device and a method for delivering a flowable ingestible medicament into the gastrointestinal tract of a user. The device includes a vibrating ingestible capsule attached to a medicament delivery compartment. The medicament delivery compartment includes a housing including a portal, a medicament reservoir, a reservoir biasing mechanism applying pressure to the reservoir, a resilient conduit extending from the reservoir to the portal, and a valve including a weight and a spring adapted, when closed, to bias the weight against the conduit so as to block flow therethrough, and, when open, to remove the weight from the conduit to allow fluid to flow through the conduit. When the vibrating agitator is in the vibration mode of operation, vibrations exerted thereby are applied to the valve biasing mechanism and periodically transition the valve between the closed operative orientation and the open operative orientation.

20 Claims, 8 Drawing Sheets

Related U.S. Application Data continuation-in-part of application No. 16/747,635, filed on Jan. 21, 2020, now Pat. No. 11,020,018.

(52) U.S. Cl.
CPC .............. *A61M 2202/0468* (2013.01); *A61M 2205/106* (2013.01); *A61M 2205/3523* (2013.01); *A61M 2205/502* (2013.01); *A61M 2205/8212* (2013.01); *A61M 2210/1053* (2013.01)

(56) References Cited

U.S. PATENT DOCUMENTS

| | | | |
|---|---|---|---|
| 4,507,115 | A | 3/1985 | Kambara et al. |
| 5,170,801 | A | 12/1992 | Casper et al. |
| 6,453,199 | B1 | 9/2002 | Kobozev |
| 6,632,216 | B2 | 10/2003 | Houzego et al. |
| 6,687,537 | B2 | 2/2004 | Bernabei |
| 6,776,165 | B2 | 8/2004 | Jin |
| 6,929,363 | B2 | 8/2005 | Sakai et al. |
| 6,984,205 | B2 | 1/2006 | Gazdzinski |
| 7,076,284 | B2 | 7/2006 | Segawa et al. |
| 7,354,397 | B2 | 4/2008 | Fujita et al. |
| 7,510,537 | B2 | 3/2009 | Imboden et al. |
| 7,686,788 | B2 | 3/2010 | Freyman et al. |
| 7,797,033 | B2 | 9/2010 | DAndrea et al. |
| 7,942,811 | B2 | 5/2011 | Segawa et al. |
| 8,021,357 | B2 * | 9/2011 | Tanaka .............. A61M 5/14276 604/890.1 |
| 8,021,384 | B2 | 9/2011 | Weiss et al. |
| 8,036,748 | B2 | 10/2011 | Zdeblick et al. |
| 8,038,600 | B2 | 10/2011 | Uchiyama et al. |
| 8,147,482 | B2 | 4/2012 | Shimizu et al. |
| 8,202,697 | B2 | 6/2012 | Holmes |
| 8,216,130 | B2 | 7/2012 | Glukhovsky et al. |
| 8,295,932 | B2 | 10/2012 | Bitton et al. |
| 8,518,022 | B2 | 8/2013 | Trovato et al. |
| 8,597,278 | B2 | 12/2013 | Trovato et al. |
| 8,701,677 | B2 | 4/2014 | Duan et al. |
| 8,755,888 | B2 | 6/2014 | Voznesensky et al. |
| 8,771,730 | B2 | 7/2014 | Navon |
| 8,945,005 | B2 | 2/2015 | Hafezi et al. |
| 9,078,799 | B2 | 7/2015 | Shohat et al. |
| 9,156,169 | B2 | 10/2015 | Duan et al. |
| 9,232,909 | B2 | 1/2016 | Duan et al. |
| 9,511,211 | B2 | 12/2016 | Tange et al. |
| 9,532,923 | B2 | 1/2017 | Shohat et al. |
| 9,538,937 | B2 | 1/2017 | Rohde et al. |
| 9,550,050 | B2 | 1/2017 | Dijksman |
| 9,572,746 | B2 | 2/2017 | Asfora |
| 9,707,150 | B2 | 7/2017 | Shabbat |
| 9,730,336 | B2 | 8/2017 | Arneson et al. |
| 9,750,923 | B2 | 9/2017 | Niichel et al. |
| 9,770,588 | B2 | 9/2017 | Bettinger |
| 9,919,152 | B2 | 3/2018 | Levine et al. |
| 10,118,035 | B2 | 11/2018 | Perez et al. |
| 10,172,598 | B2 | 1/2019 | Amoako-Tuffour et al. |
| 10,369,463 | B2 | 8/2019 | Barney et al. |
| 10,537,720 | B2 | 1/2020 | Ben-Tsur |
| 10,543,348 | B2 | 1/2020 | Ben-Tsur |
| 10,814,113 | B2 | 10/2020 | Ben-Tsur et al. |
| 10,874,339 | B2 | 12/2020 | Chavan et al. |
| 10,888,277 | B1 | 1/2021 | Ben-Tsur et al. |
| 10,905,378 | B1 | 2/2021 | Ben-Tsur et al. |
| 11,020,018 | B2 | 6/2021 | Ben-Tsur et al. |
| 11,116,658 | B2 | 9/2021 | Ilan |
| 11,351,111 | B2 | 6/2022 | Kelrich |
| 2002/0099310 | A1 | 7/2002 | Kimchy et al. |
| 2002/0132226 | A1 | 9/2002 | Nair et al. |
| 2003/0020810 | A1 | 1/2003 | Takizawa et al. |
| 2004/0030454 | A1 | 2/2004 | Kim et al. |
| 2004/0253304 | A1 | 12/2004 | Gross et al. |
| 2004/0267240 | A1 | 12/2004 | Gross et al. |
| 2005/0058701 | A1 | 3/2005 | Gross et al. |
| 2005/0085696 | A1 | 4/2005 | Uchiyama et al. |
| 2005/0148847 | A1 | 7/2005 | Uchiyama et al. |
| 2005/0177069 | A1 | 8/2005 | Takizawa et al. |
| 2006/0137934 | A1* | 6/2006 | Kurth .............. A61F 11/08 181/135 |
| 2006/0169293 | A1 | 8/2006 | Yokoi et al. |
| 2006/0211963 | A1 | 9/2006 | Spirk et al. |
| 2006/0270899 | A1 | 11/2006 | Amirana |
| 2006/0276729 | A1 | 12/2006 | Reed et al. |
| 2007/0015952 | A1 | 1/2007 | Chang et al. |
| 2007/0032699 | A1 | 2/2007 | Segawa |
| 2007/0238940 | A1 | 10/2007 | Amirana |
| 2008/0051635 | A1 | 2/2008 | Tanaka et al. |
| 2008/0161639 | A1 | 7/2008 | Katayama et al. |
| 2008/0188837 | A1 | 8/2008 | Belsky et al. |
| 2008/0269664 | A1 | 10/2008 | Trovato et al. |
| 2008/0275430 | A1 | 11/2008 | Belsky et al. |
| 2008/0281238 | A1 | 11/2008 | Oohashi et al. |
| 2009/0281380 | A1 | 11/2009 | Miller et al. |
| 2009/0306633 | A1* | 12/2009 | Trovato .............. A61B 1/041 604/891.1 |
| 2009/0318841 | A1 | 12/2009 | Shohat et al. |
| 2010/0049012 | A1 | 2/2010 | Dijksman et al. |
| 2010/0217079 | A1 | 8/2010 | Tichy |
| 2010/0222670 | A1 | 9/2010 | Demierre et al. |
| 2011/0208011 | A1 | 8/2011 | Ben-Horin |
| 2011/0319727 | A1 | 12/2011 | Ishihara |
| 2013/0158452 | A1 | 6/2013 | Juto et al. |
| 2013/0253387 | A1 | 9/2013 | Bonutti et al. |
| 2013/0267788 | A1 | 10/2013 | Duan et al. |
| 2014/0221741 | A1 | 8/2014 | Wang et al. |
| 2015/0011829 | A1 | 1/2015 | Wang et al. |
| 2015/0018614 | A1 | 1/2015 | Duan et al. |
| 2015/0018615 | A1 | 1/2015 | Duan et al. |
| 2015/0065926 | A1 | 3/2015 | Nakamura et al. |
| 2015/0073315 | A1 | 3/2015 | Shabbat |
| 2015/0223727 | A1 | 8/2015 | Kimchy et al. |
| 2015/0313792 | A1 | 11/2015 | Shohat et al. |
| 2015/0380140 | A1 | 12/2015 | Duan et al. |
| 2016/0183878 | A1 | 6/2016 | Weast et al. |
| 2016/0287058 | A1 | 10/2016 | Ye et al. |
| 2016/0303133 | A1 | 10/2016 | Dudley et al. |
| 2016/0310357 | A1 | 10/2016 | Duan et al. |
| 2017/0020374 | A1 | 1/2017 | Duan et al. |
| 2017/0035407 | A1 | 2/2017 | Duan et al. |
| 2017/0035520 | A1 | 2/2017 | Duan et al. |
| 2017/0135897 | A1 | 5/2017 | Shohat et al. |
| 2017/0273863 | A1 | 9/2017 | Shabbat |
| 2017/0296425 | A1 | 10/2017 | Duan et al. |
| 2017/0296428 | A1 | 10/2017 | Duan et al. |
| 2017/0340242 | A1 | 11/2017 | Duan |
| 2018/0055597 | A1 | 3/2018 | Duan et al. |
| 2018/0070857 | A1 | 3/2018 | Jones |
| 2018/0084975 | A1 | 3/2018 | Duan et al. |
| 2018/0168490 | A1 | 6/2018 | Jones et al. |
| 2019/0224070 | A1 | 7/2019 | Ben-Tsur et al. |
| 2019/0307999 | A1 | 10/2019 | Ben-Tsur |
| 2019/0308002 | A1 | 10/2019 | Ben-Tsur |
| 2020/0214592 | A1 | 7/2020 | Ben-Tsur et al. |
| 2020/0229733 | A1 | 7/2020 | Ben Tzur et al. |
| 2020/0246216 | A1 | 8/2020 | Molnar |
| 2020/0315541 | A1 | 10/2020 | Ben-Tsur et al. |
| 2021/0023357 | A1 | 1/2021 | Ben-Tsur |
| 2021/0066998 | A1 | 3/2021 | Molnar |
| 2021/0196296 | A1 | 7/2021 | Ben-Tsur et al. |
| 2021/0236381 | A1 | 8/2021 | Ben-Tsur et al. |
| 2021/0290483 | A1 | 9/2021 | Molnar et al. |
| 2021/0322741 | A1 | 10/2021 | Ben-Tsur et al. |
| 2021/0386316 | A1 | 12/2021 | Ben-Tsur et al. |
| 2022/0054352 | A1 | 2/2022 | Shohat et al. |

FOREIGN PATENT DOCUMENTS

| | | |
|---|---|---|
| CN | 102743174 A | 10/2012 |
| CN | 102743175 A | 10/2012 |
| CN | 102743176 A | 10/2012 |
| CN | 202483565 U | 10/2012 |
| CN | 102813515 A | 12/2012 |
| CN | 102860810 A | 1/2013 |

(56) References Cited

FOREIGN PATENT DOCUMENTS

| | | |
|---|---|---|
| CN | 202699138 U | 1/2013 |
| CN | 202821355 U | 3/2013 |
| CN | 202843564 U | 4/2013 |
| CN | 202843608 U | 4/2013 |
| CN | 202875332 U | 4/2013 |
| CN | 103222842 A | 7/2013 |
| CN | 203634116 U | 6/2014 |
| CN | 104898850 A | 9/2015 |
| CN | 105025245 A | 11/2015 |
| CN | 105079970 A | 11/2015 |
| CN | 105380777 A | 3/2016 |
| CN | 105411505 A | 3/2016 |
| CN | 205108749 U | 3/2016 |
| CN | 205286889 U | 3/2016 |
| CN | 105939451 A | 9/2016 |
| CN | 105942959 A | 9/2016 |
| CN | 105996961 A | 10/2016 |
| CN | 106056588 A | 10/2016 |
| CN | 106097335 A | 11/2016 |
| CN | 106137760 A | 11/2016 |
| CN | 106204599 A | 12/2016 |
| CN | 205758500 U | 12/2016 |
| CN | 106373137 A | 2/2017 |
| CN | 205913317 U | 2/2017 |
| CN | 205928774 U | 2/2017 |
| CN | 106923787 A | 7/2017 |
| CN | 106934799 A | 7/2017 |
| CN | 107174188 A | 9/2017 |
| CN | 107233580 A | 10/2017 |
| CN | 107240091 A | 10/2017 |
| CN | 107375951 A | 11/2017 |
| EP | 2987447 A1 | 2/2016 |
| EP | 2995240 A1 | 3/2016 |
| JP | 2001062397 A | 3/2001 |
| JP | 2002163359 A | 6/2002 |
| JP | 2005052502 A | 3/2005 |
| JP | 2010503451 A | 2/2010 |
| JP | 2010246703 A | 11/2010 |
| JP | 2013535756 A | 9/2013 |
| WO | 2006025013 A1 | 3/2006 |
| WO | 2007013059 A2 | 2/2007 |
| WO | 2008012700 A1 | 1/2008 |
| WO | 2008035329 A2 | 3/2008 |
| WO | 2009063375 A1 | 5/2009 |
| WO | 2009/153973 A1 | 12/2009 |
| WO | 2013121276 A1 | 8/2013 |
| WO | 2018055487 A1 | 3/2018 |

OTHER PUBLICATIONS

Machine Translation (by Google Patents) for CN 105380777 published on Mar. 9, 2016.
Machine Translation (by Google Patents) for CN 205286889 published on Mar. 9, 2016.
Machine Translation (by Google Patents) for JP 2002163359 published on Jun. 7, 2002.
Machine Translation (by Google Patents) for JP 2005052502 published on Mar. 3, 2005.
Machine Translation (by Google Patents) for JP 2010246703 published on Nov. 4, 2010.
Machine Translation (by Google Patents) for JP 2013535756 published on Sep. 12, 2013.
Smart capsule to target colon diseases, Ben Gruber, Sep. 30, 2015, Reuters Health News.
Advanced Delivery Devices—IntelliCap: An Intelligent, Electronic Capsule for Oral Drug Delivery & Development', Drug Development & Delivery, Apr. 2013.
Machine Translation (by Google Patents) for CN 102743174 published on Oct. 24, 2012.
Machine Translation (by Google Patents) for CN 102743175 published on Oct. 24, 2012.
Machine Translation (by Google Patents) for CN 102743176 published on Oct. 24, 2012.
Machine Translation (by Google Patents) for CN 102813515 published on Dec. 12, 2012.
Machine Translation (by Google Patents) for CN 102860810 published on Jan. 9, 2013.
Machine Translation (by Google Patents) for CN 03222842 published on Jul. 31, 2013.
Machine Translation (by Google Patents) for CN 104898850 published on Sep. 9, 2015.
Machine Translation (by Google Patents) for CN 105025245 published on Nov. 4, 2015.
Machine Translation (by Google Patents) for CN 105079970 published on Nov. 25, 2015.
Machine Translation (by Google Patents) for CN 105411505 published on Mar. 23, 2016.
Machine Translation (by Google Patents) for CN 105939451 published on Sep. 14, 2016.
Machine Translation (by Google Patents) for CN 105942959 published on Sep. 21, 2016.
Machine Translation (by Google Patents) for CN 105996961 published on Oct. 12, 2016.
Machine Translation (by Google Patents) for CN 106056588 published on Oct. 26, 2016.
Machine Translation (by Google Patents) for CN 106097335 published on Nov. 9, 2016.
Machine Translation (by Google Patents) for CN 106137760 published on Nov. 23, 2016.
Machine Translation (by Google Patents) for CN 106204599 published on Dec. 7, 2016.
Machine Translation (by Google Patents) for CN 106373137 published on Feb. 1, 2017.
Machine Translation (by Google Patents) for CN 106923787 published on Jul. 7, 2017 .
Machine Translation (by Google Patents) for CN 106934799 published on Jul. 7, 2017.
Machine Translation (by Google Patents) for CN 107174188 published on Sep. 19, 2017.
Machine Translation (by Google Patents) for CN 107233580 published on Oct. 10, 2017.
Machine Translation (by Google Patents) for CN 107240091 published on Oct. 10, 2017.
Machine Translation (by Google Patents) for CN 107375951 published on Nov. 24, 2017.
Machine Translation (by Google Patents) for CN 1829466 published on Sep. 6, 2006.
Machine Translation (by Google Patents) for CN 202483565 published on Oct. 10, 2012.
Machine Translation (by Google Patents) for CN 202699138 published on Jan. 30, 2013.
Machine Translation (by Google Patents) for CN 202821355 published on Mar. 27, 2013.
Machine Translation (by Google Patents) for CN 202843564 published on Apr. 3, 2013.
Machine Translation (by Google Patents) for CN 202843608 published on Apr. 3, 2013.
Machine Translation (by Google Patents) for CN 202875332 published on Apr. 17, 2013.
Machine Translation (by Google Patents) for CN 203634116 published on Jun. 11, 2014.
Machine Translation (by Google Patents) for CN 205108749 published on Mar. 30, 2016.
Machine Translation (by Google Patents) for CN 205758500 published on Dec. 7, 2016.
Machine Translation (by Google Patents) for CN 205913317 published on Feb. 1, 2017.
Machine Translation (by Google Patents) for CN 205928774 published on Feb. 8, 2017.
Machine Translation (by Google Patents) for JP 2001062397 published on Mar. 13, 2001.
Machine Translation (by Google Patents) for JP 2010503451 published on Feb. 4, 2010.
Co-pending U.S. Appl. No. 15/882,283, filed Jan. 29, 2018.
Co-pending U.S. Appl. No. 16/403,553, filed May 5, 2019.
Abandoned U.S. Appl. No. 15/882,552, filed Jan. 29, 2018.

(56) References Cited

OTHER PUBLICATIONS

Co-pending U.S. Appl. No. 16/823,035, filed Mar. 18, 2020.
Co-pending U.S. Appl. No. 16/377,213, filed Apr. 7, 2019.
Co-pending U.S. Appl. No. 17/038,226, filed Sep. 30, 2020.

* cited by examiner

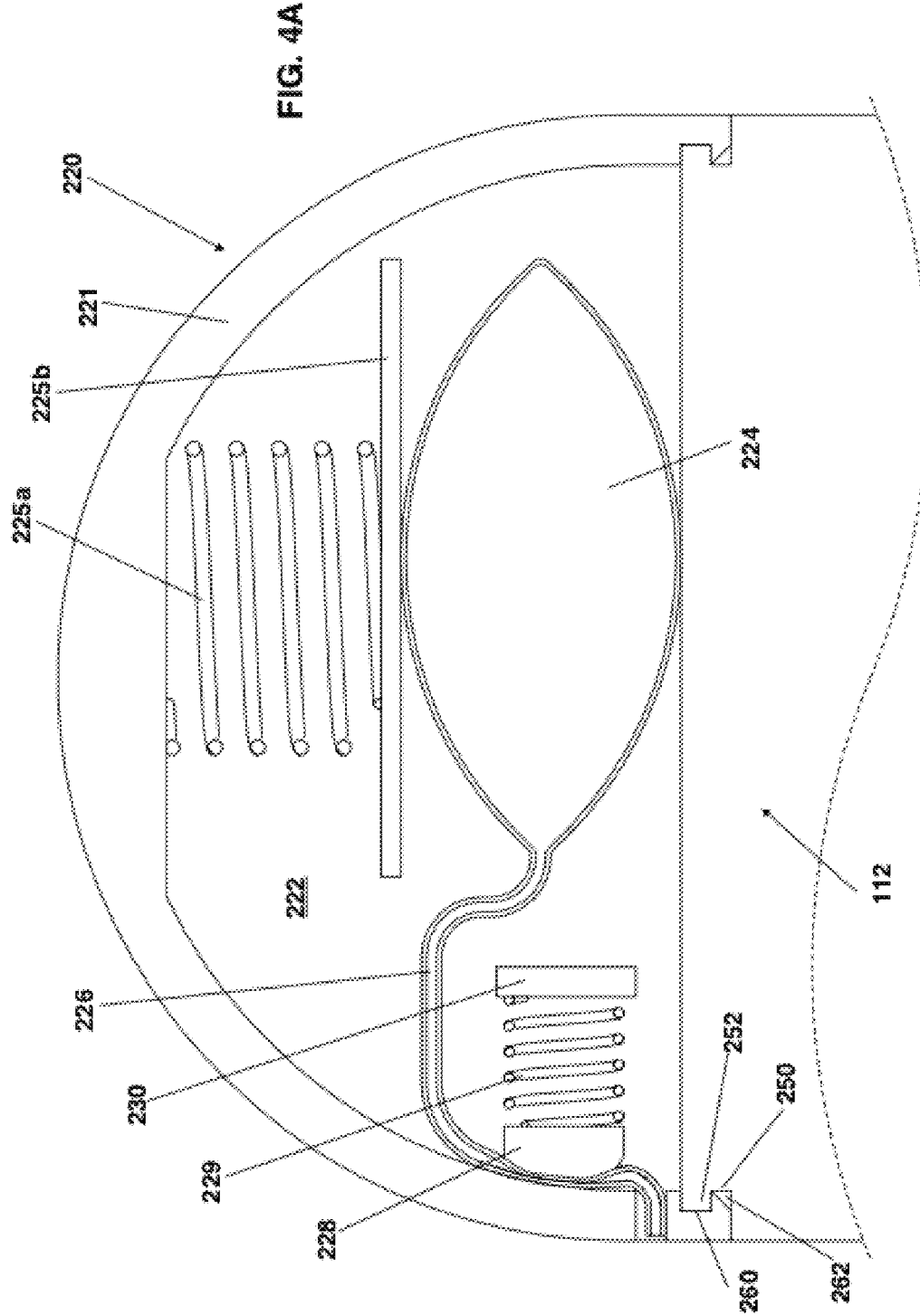

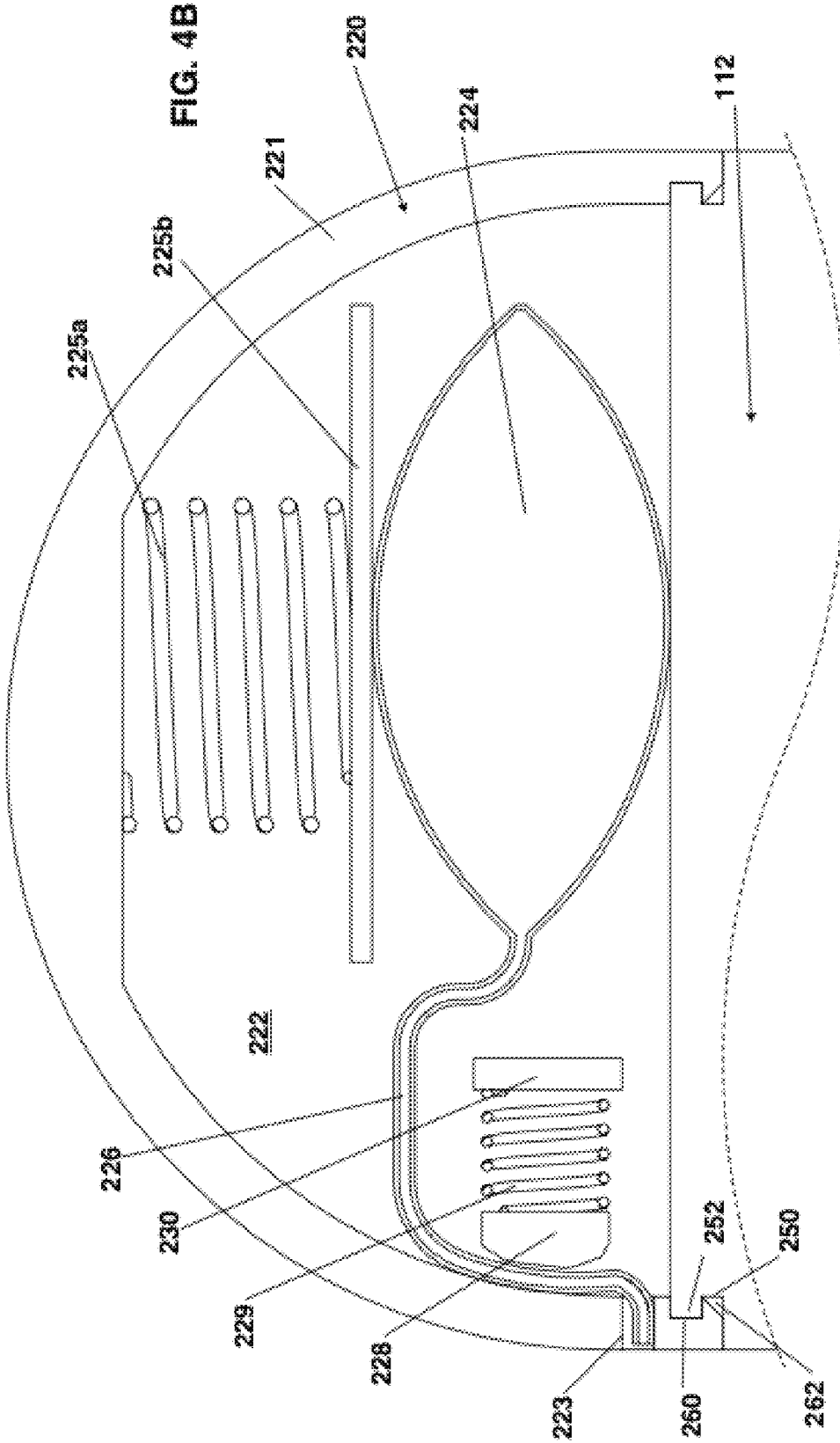

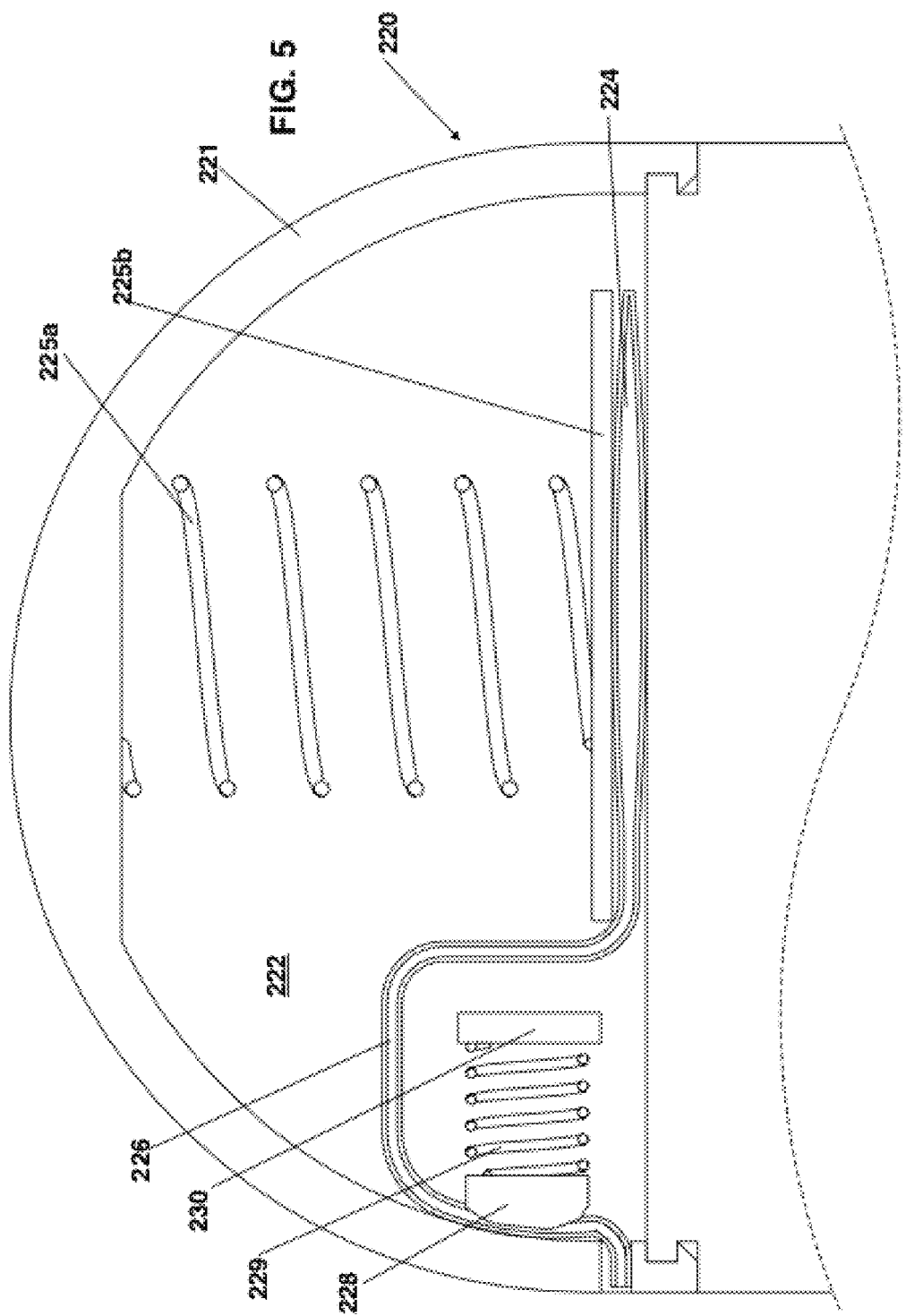

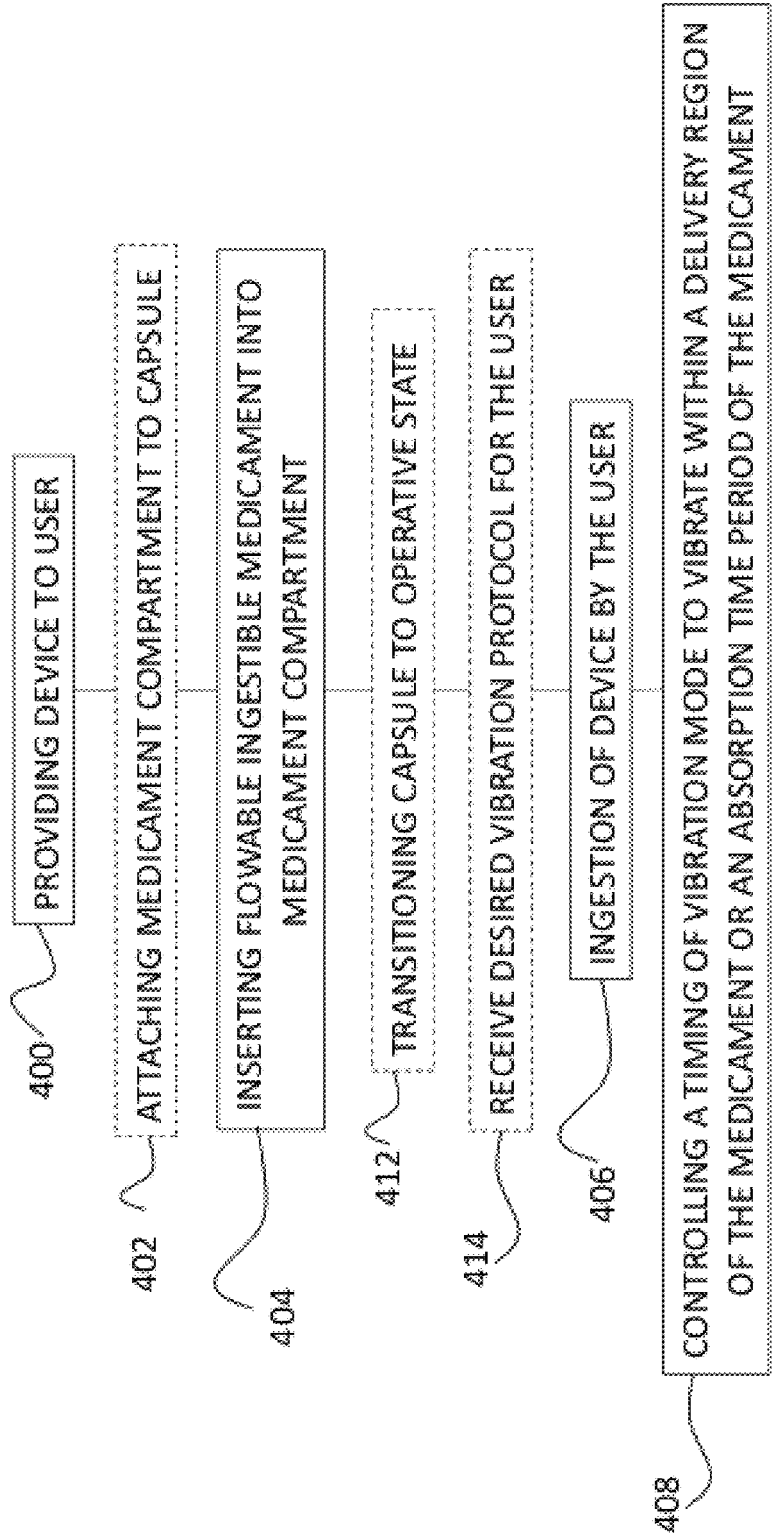

DEVICE AND METHOD FOR DELIVERING A FLOWABLE INGESTIBLE MEDICAMENT INTO THE GASTROINTESTINAL TRACT OF A USER

RELATED APPLICATIONS

The present application is a Continuation In Part (CIP) of U.S. patent application Ser. No. 16/747,635 filed Jan. 21, 2020 and entitled DEVICE AND METHOD FOR DELIVERING A FLOWABLE INGESTIBLE MEDICAMENT INTO THE GASTROINTESTINAL TRACT OF A USER and is a CIP of PCT Patent Application No. PCT/IB2020/050433 filed Jan. 21, 2020 and entitled DEVICE AND METHOD FOR DELIVERING A FLOWABLE INGESTIBLE MEDICAMENT INTO THE GASTROINTESTINAL TRACT OF A USER, both of which gain priority from GB Patent Application Number 1900780.6 filed Jan. 21, 2019 and entitled DEVICE AND METHOD FOR DELIVERING A FLOWABLE INGESTIBLE MEDICAMENT INTO THE GASTROINTESTINAL TRACT OF A USER, all of which are incorporated herein by reference as if fully set forth herein.

FIELD OF THE INVENTION

The present invention relates in general to devices and methods for delivery of a flowable ingestible medicament into the body of a user, and specifically to devices and methods for such delivery of a flowable ingestible medicament triggered by vibration of a vibrating capsule.

SUMMARY OF THE INVENTION

In accordance with an embodiment of the present invention, there is provided a device for delivering a flowable ingestible medicament into the gastrointestinal tract of a user, the device including:
  a housing including a first housing portion and a second housing portion, the second housing portion having a portal formed therein;
  a vibrating agitator disposed within the housing and adapted such that, in a vibration mode of operation, the housing exerts vibrations on an environment surrounding the vibrating ingestible capsule;
  a power supply disposed within the housing and adapted to power the vibrating agitator; and
  a control element adapted to activate the vibrating agitator to be operative in the vibration mode of operation;
  a flexible and collapsible medicament reservoir dimensioned to contain the flowable ingestible medicament;
  a reservoir biasing mechanism adapted to apply pressure to the flexible and collapsible medicament reservoir;
  a conduit extending from the medicament reservoir to the portal, and sealing the portal; and
  a valve including a weight and a valve biasing mechanism adapted, in a closed operative orientation, to bias the weight against the conduit so as to block flow through the conduit, and in an open operative orientation to remove the weight from the conduit so as to allow fluid to flow through the conduit,
  wherein the valve is functionally associated with at least one of the housing and the vibrating agitator, such that when the vibrating agitator is in the vibration mode of operation, at least some of the vibrations exerted by the vibrating agitator or by the housing are applied to the valve biasing mechanism and periodically transition the valve between the closed operative orientation and the open operative orientation.

In some embodiments, when the vibrating agitator is in the vibration mode of operation and the valve is in the open operative orientation, pressure applied by the reservoir biasing mechanism to the reservoir causes the flowable ingestible medicament to flow from the reservoir, via the conduit and the portal, to an environment surrounding the device.

In some embodiments, at least one vibration parameter of the vibrating agitator is set so as to promote transitioning of the valve between the closed operative orientation and the open operative orientation. In some embodiments, at least one vibration parameter of the vibrating agitator is set so as to promote absorption of the ingestible medicament into the bloodstream of the user.

In some embodiments, at least one valve parameter of the valve is set such that the valve functions as a gear reducer, opening and closing at a frequency smaller than a frequency of the vibrating agitator. In some embodiments, the at least one valve parameter includes a mass of the weight, a length of the valve biasing mechanism, and a spring constant of the valve biasing mechanism.

In some embodiments, the at least one vibration parameter includes at least one of a vibration frequency, a cumulative vibration duration, a number of vibration cycles per time unit, a duration of a vibration duration within a vibration cycle, a duration of a repose duration within a vibration cycle, a total duration of a single vibration cycle, and a net force exerted by the housing on the environment.

In some embodiments, the first housing portion is a sealed housing portion accommodating the vibrating agitator, the power supply, and the control element, the second housing portion accommodates the flexible and collapsible medicament reservoir, the reservoir biasing mechanism, the conduit, and the valve, the first housing portion and the second housing portion are separate elements, which are attached to each other to form the housing, and the valve is functionally associated with the first housing portion such that when the vibrating agitator is in the vibration mode of operation, at least some of the vibrations exerted by the first housing portion are applied to the valve biasing mechanism and periodically transition the valve between the closed operative orientation and the open operative orientation.

In some embodiments, the second housing portion is fixedly attached to the first housing portion. In some embodiments, the second housing portion is attached to the first housing portion by snap fit engagement. In some embodiments, the second housing portion is attached to the first housing portion by threaded engagement. In some embodiments, the second housing portion is attached to the first housing portion by adhering. In some embodiments, the second housing portion is attached to the first housing portion by soldering.

In some embodiments, the first and second housing portions form a single housing element including the portal and defining a single hollow, the single hollow accommodating the vibrating agitator, the power supply, the control element, the flexible and collapsible medicament reservoir, the reservoir biasing mechanism, and the flexible and resilient conduit.

In some embodiments, a hollow of the second housing portion has a volume in the range of 200 $mm^3$ to 3000 $mm^3$, 200 $mm^3$ to 800 $mm^3$, 100 $mm^3$ to 600 $mm^3$, 400 $mm^3$ to 1000 $mm^3$, 700 $mm^3$ to 1500 $mm^3$, or 1400 $mm^3$ to 3000 $mm^3$ In some embodiments, the flexible and collapsible medicament reservoir has a maximal volume in the range of 0.5 ml to 15 ml. In some embodiments, the flexible and collapsible medicament reservoir has a Young's modulus smaller than 1 GPa. In some embodiments, the flexible and collapsible medicament reservoir is formed of a material selected from the group consisting of: silicone rubber, natural rubber, Polyethylene, and PVC.

In some embodiments, the reservoir biasing mechanism includes a reservoir spring terminating in a pressure applying surface, the pressure applying surface engaging an exterior surface of the medicament reservoir. In some embodiments, the reservoir spring is anchored to the second housing portion. In some embodiments, the reservoir biasing mechanism has a spring constant in the range of 1 N/m to 200 N/m.

In some embodiments, the conduit is integrally formed with the medicament reservoir. In some embodiments, the conduit is formed of a different material than the medicament reservoir. In some embodiments, a recovery time of the conduit is at most 0.1 seconds.

In some embodiments, the vibrating agitator has a frequency f, and a recovery time of the conduit is at most equal to 1/f. In some embodiments, the valve biasing mechanism has a frequency fv of moving from the open operative orientation to the closed operative orientation and back to the open operative orientation, and a recovery time of the conduit is at most equal to 1/fv.

In some embodiments, the conduit has a diameter in the range of 0.01 mm to 0.9 mm. In some embodiments, the conduit has a length in the range of 3 mm to 25 mm. In some embodiments, the conduit is at least one of, and optionally both of, flexible and resilient.

In some embodiments, the valve biasing mechanism is anchored to the first housing portion. In some embodiments, the valve biasing mechanism is anchored to the second housing portion. In some embodiments, the valve biasing mechanism has a spring constant in the range of 0.1 N/m to 5 N/m.

In some embodiments, the weight has a mass in the range of 0.1 grams to 2 grams. In some embodiments, the weight includes the vibrating agitator.

In some embodiments, the vibrations exerted by the vibrating agitator are transferred, through an anchoring point of the valve biasing mechanism, to the valve biasing mechanism, thereby causing rocking of the valve biasing mechanism resulting in the periodic transitioning of the valve between the closed operative orientation and the open operative orientation.

In some embodiments, the control element is adapted to control a timing or activation delay of the vibration mode of operation such that the vibration mode of operation at least partially transpires within a region of the gastrointestinal tract in which the flowable ingestible medicament is absorbable by the body of the user.

In some embodiments, the control element is adapted to control a timing or activation delay of the vibrating mode of operation such that the vibration mode of operation at least partially transpires during at least one of an estimated absorption time period and an actual absorption time period of the flowable ingestible medicament released from the reservoir, via the conduit and the portal, into the gastrointestinal tract of the user.

In some embodiments, the control element is adapted to activate the vibrating agitator to be operative in the vibration mode of operation in response to receipt of an activation input.

In some embodiments, the device further includes at least one sensor adapted to provide the activation input to the control element. In some embodiments, the at least one sensor forms part of the vibrating ingestible capsule.

In some embodiments, the at least one sensor includes an illumination sensor, adapted to provide an input indicating transition of the device from an illuminated environment to a dark environment.

In some embodiments, the at least one sensor includes a pressure sensor, adapted to provide an input indicating pressure applied to the device, which pressure is indicative of the device moving through a pharynx of the user.

In some embodiments, the at least one sensor includes a temperature sensor, adapted to provide an input indicating transition of the device from an area with ambient temperature to an area with a human body temperature.

In some embodiments, the at least one sensor includes an accelerometer, adapted to provide an input in response to a detected activation motion carried out with the device.

In some embodiments, the at least one sensor includes a moisture sensor, adapted to provide an input indicating transition of the device from a dry environment to a humid environment.

In some embodiments, the device is functionally associated with a control unit remote from the device, and the control element is adapted to receive the activation input from the control unit.

In some embodiments, the control element is adapted to receive the activation input following ingesting of the device.

In some embodiments, the control element is adapted to receive the activation input prior to ingesting of the device.

In some embodiments, the control element is adapted to receive the activation input by receiving a vibration protocol to be used by the control element to control operation of the vibrating agitator.

In some embodiments, the vibrating agitator includes at least a radial agitation mechanism adapted, in the vibration mode of operation, to exert radial forces on the housing, in a radial direction with respect to a or the longitudinal axis of the housing, thereby to cause the vibrations exerted by the housing.

In some embodiments, the vibrating agitator includes at least an axial agitation mechanism adapted, in the vibration mode of operation, to exert axial forces on the housing, in an axial direction with respect to a or the longitudinal axis of the housing, thereby to cause the vibrations exerted by the housing.

In some embodiments, the vibrating agitator includes a radial agitation mechanism adapted, in the vibration mode of operation, to exert radial forces on the housing, in a radial direction with respect to a or the longitudinal axis of the housing, and a separate axial agitation mechanism adapted, in the vibration mode of operation, to exert axial forces on the housing, in an axial direction with respect to a or the longitudinal axis of the housing.

In some embodiments, the vibrating agitator includes a single agitation mechanism adapted, in the vibration mode of operation, to exert radial forces on the housing in a radial direction with respect to a or the longitudinal axis of the housing, and to exert axial forces on the housing, in an axial direction with respect to the longitudinal axis of the housing.

In some embodiments, the control element is adapted to control the vibrating agitator such that the vibrating mode of operation includes a plurality of cycles, each of the cycles including a vibration duration followed by a repose duration, wherein the housing exerts the vibrations during the vibration duration. In some embodiments, the repose duration is greater than the vibration duration.

In some embodiments, the vibration duration is in the range of 0.1 second to 10 seconds, 1 second to 10 seconds, 1 second to 9 seconds, 2 seconds to 9 seconds, 3 seconds to 9 seconds, 3 seconds to 8 seconds, 3 seconds to 7 seconds, 3 seconds to 6 seconds, 4 seconds to 6 seconds, or 5 seconds to 6 seconds.

In some embodiments, the repose duration is in the range of 1 second to 180 seconds, 3 seconds to 180 seconds, 5 seconds to 180 seconds, 5 seconds to 150 seconds, 5 seconds to 120 seconds, 8 seconds to 100 seconds, 8 seconds to 30 seconds, 10 seconds to 80 seconds, 10 seconds to 70 seconds, 10 seconds to 60 seconds, 10 seconds to 50 seconds, 10 seconds to 40 seconds, 10 seconds to 30 seconds, 10 seconds to 20 seconds, or 15 seconds to 20 seconds.

In some embodiments, a duration of each of the plurality of cycles is in the range of 1.1 seconds to 200 seconds, 5 seconds to 200 seconds, 10 seconds to 200 seconds, 10 seconds to 150 seconds, 10 seconds to 100 seconds, 10 seconds to 80 seconds, 10 seconds to 50 seconds, 10 seconds to 40 seconds, 10 seconds to 30 seconds, 15 seconds to 50 seconds, 15 seconds to 40 seconds, 15 seconds to 30 seconds, or 15 seconds to 25 seconds.

In some embodiments, the control element is adapted to control the vibrating agitator such that a cumulative duration of the vibrating mode of operation is in the range of 1 hour to 12 hours, 2 hours to 10 hours, 2 hours to 8 hours, 2 hours to 6 hours, 2 hours to 4 hours, or 2 hours to 3 hours.

In some embodiments, the vibrating agitator is configured to exert forces on the housing of the vibrating ingestible capsule, such that a net force exerted by the housing on the environment thereof is in the range of 50 grams force (gf) to 600 gf, 50 gf to 550 gf, 100 gf to 550 gf, 100 gf to 500 gf, 150 gf to 500 gf, 200 gf to 500 gf, or 200 gf to 450 gf.

In some embodiments, the vibrating agitator is configured to exert the forces on the housing to attain a housing vibrational frequency within a range of 10 Hz to 650 Hz, 15 Hz to 600 Hz, 20 Hz to 550 Hz, 30 Hz to 550 Hz, 50 Hz to 500 Hz, 70 Hz to 500 Hz, 100 Hz to 500 Hz, 130 Hz to 500 Hz, or 150 Hz to 500 Hz.

In some embodiments, the device further includes the flowable ingestible medicament disposed within the medicament reservoir.

In some embodiments, the flowable ingestible medicament has a viscosity in the range of 100 Pa·s to 1000 Pa·s.

In some embodiments, the flowable ingestible medicament is absorbable in the stomach of the user. In some embodiments, the flowable ingestible medicament is absorbable in the small intestine of the user.

In some embodiments, the flowable ingestible medicament is suitable for treatment of one or more symptom or disease, selected from the group consisting of: Parkinsonism; Parkinson's Disease; progressive supranuclear palsy; corticobasal degeneration; multiple system atrophy; Parkinson-plus syndromes; any neurodegenerative disease in which the subject exhibits at least one, at least two, or at least three of the classical features of Parkinson's disease: tremor, postural instability, and akinesia or bradykesia; any neurodegenerative disease in which the subject positively responds to a dopaminergic treatment; any neurodegenerative disease in which the particular subject positively responds to an anticholinergic treatment; Constipation; Crohn's disease; Gastroparesis; irritable bowel syndrome (IBS); diarrhea or loose bowel movements; colitis; Hirschsprung's disease; Dyspepsia; and dysphagia.

In some embodiments, the flowable ingestible medicament includes or includes an ingestible medicament selected from the group consisting of: Levodopa; at least one dopaminergic agent; at least one catecholamine precursor; a dopamine precursor; at least one dopamine precursor agent; (L)-3,4-dihydroxyphenylalanine; N-methyl-N-(2-propynyl)-2-methyl-1-phenylethyl-2-amine; tyrosine hydroxylase; apomorphine; at least one anticholinergic agent; at least one agent selected to antagonize at least one cholinergic receptor; benzhexol; orphenadrine; at least one selective allosteric potentiator of metabotropic glutamate receptor 4 (mGluR4); N-phenyl-7-(hydroxylimino)cyclopropa[b]chromen-1a-carboxamide; at least one osmotic agent; magnesium citrate; magnesium hydroxide; polyethylene glycol; sodium phosphate; MiraLAX®; at least one contraction stimulating agent; bisacodyl; senna; Correctol; Ducodyl; Dulcolax; Senexon; Senokot; at least one stool softening agent; docusate sodium; Colace; Linaclotide; Lactulose; Lubiprostone; Plecanatide; Prucaltride; Loperamide; and bismuth subsalicylate.

In accordance with another embodiment of the present invention, there is provided a method of delivering an ingestible medicament into a gastrointestinal tract of a user, the method including:

providing to the user the device as described hereinabove, for ingestion by the user;

following the user ingesting the device, controlling the vibrating agitator such that the vibration mode of operation at least partially transpires within a region of the gastrointestinal tract in which the flowable ingestible medicament is absorbable by the body of the user, thereby to cause the periodic transitioning of the valve between the closed operative orientation and the open operative orientation, and delivery of the flowable ingestible medicament from the reservoir, via the conduit and the portal, into the environment surrounding the device.

In some embodiments, controlling the vibrating agitator further includes controlling the vibrating agitator such that the vibration mode of operation at least partially transpires within at least one of an estimated absorption time period and an actual absorption time period of the ingestible medicament within the gastrointestinal tract of the user.

In accordance with yet another embodiment of the present invention, there is provided a medicament delivery compartment, adapted to be attached to a vibrating ingestible capsule having a first housing portion and adapted to operate in a vibrating mode of operation, for delivery of a flowable ingestible medicament into the gastrointestinal tract of a user, the medicament delivery compartment including:

a second housing portion adapted to be attached to the first housing portion of the vibrating ingestible capsule, and having a portal formed therein;

a flexible and collapsible medicament reservoir dimensioned to contain the flowable ingestible medicament;

a reservoir biasing mechanism adapted to apply pressure to the flexible and collapsible medicament reservoir;

a conduit extending from the medicament reservoir to the portal, and sealing the portal; and a valve including a weight and a valve biasing mechanism adapted, in a closed operative orientation, to bias the weight against the conduit so as to block flow through the conduit, and in an open operative orientation to remove the weight from the conduit so as to allow fluid to flow through the conduit.

In some embodiments, the valve is configured to be in the open operative orientation and to enable flow through the conduit when the vibrating ingestible capsule is in the vibration mode of operation. In some embodiments, at least one valve parameter of the valve is set such that the valve functions as a gear reducer, opening and closing at a frequency smaller than a frequency of vibration of the vibrating ingestible capsule. In some embodiments, the at least one valve parameter includes a mass of the weight, a length of the valve biasing mechanism, and a spring constant of the valve biasing mechanism.

In some embodiments, the second housing portion includes an attachment mechanism for mutual attachment to a corresponding attachment mechanism of the first housing portion of the vibrating ingestible capsule. In some embodiments, the second housing portion is adapted to be fixedly attached to the first housing portion. In some embodiments, the second housing portion is adapted to be attached to the first housing portion by snap fit engagement. In some embodiments, the second housing portion is adapted to be attached to the first housing portion by threaded engagement. In some embodiments, the second housing portion is adapted to be attached to the first housing portion by adhering. In some embodiments, the second housing portion is adapted to be attached to the first housing portion by soldering.

In some embodiments, a hollow formed in the second housing portion has a volume in the range of 200 mm$^3$ to 3000 mm$^3$, 200 mm$^3$ to 800 mm$^3$, 100 mm$^3$ to 600 mm$^3$, 400 mm$^3$ to 1000 mm$^3$, 700 mm$^3$ to 1500 mm$^3$, or 1400 mm$^3$ to 3000 mm$^3$.

In some embodiments, the flexible and collapsible medicament reservoir has a maximal volume in the range of 1 mm$^3$ to 600 mm$^3$, 1 mm$^3$ to 10 mm$^3$, 5 mm$^3$ to 20 mm$^3$, 15 mm$^3$ to 50 mm$^3$, 30 mm$^3$ to 200 mm$^3$, 100 mm$^3$ to 400 mm$^3$, or 300 mm$^3$ to 600 mm$^3$ In some embodiments, the flexible and collapsible medicament reservoir has a Young's modulus smaller than 1 GPa. In some embodiments, the flexible and collapsible medicament reservoir is formed of a material selected from the group consisting of: silicone rubber, natural rubber, Polyethylene, and PVC.

In some embodiments, the reservoir biasing mechanism includes a reservoir spring terminating in a pressure applying surface, the pressure applying surface engaging an exterior surface of the medicament reservoir. In some embodiments, the reservoir spring is anchored to the second housing portion. In some embodiments, the reservoir biasing mechanism has a spring constant in the range of 1 N/m to 200 N/m.

In some embodiments, the conduit is integrally formed with the medicament reservoir. In some embodiments, the conduit is formed of a different material than the medicament reservoir.

In some embodiments, a recovery time of the conduit is at most 0.1 seconds. In some embodiments, the vibrating ingestible capsule is adapted to vibrate at a frequency f, and a recovery time of the conduit is at most equal to 1/f. In some embodiments, the valve biasing mechanism has a frequency fv of moving between the closed operative orientation and the open operative orientation, and a recovery time of the conduit is at most equal to 1/fv.

In some embodiments, the conduit has a diameter in the range of 0.01 mm to 0.9 mm. In some embodiments, the conduit has a length in the range of 3 mm to 25 mm. In some embodiments, the conduit is at least one of, and optionally both of, flexible and resilient.

In some embodiments, the valve biasing mechanism is adapted to be anchored to the vibrating ingestible capsule. In some embodiments, the valve biasing mechanism is anchored to the second housing portion. In some embodiments, the valve biasing mechanism has a spring constant in the range of 0.1 N/m to 5 N/m.

In some embodiments, the weight has a mass in the range of 0.1 grams to 2 grams.

In some embodiments, the medicament delivery compartment further includes the flowable ingestible medicament disposed within the medicament reservoir.

In some embodiments, the flowable ingestible medicament has a viscosity in the range of 100 Pa·s to 1000 Pa·s.

In some embodiments, the flowable ingestible medicament is absorbable in the stomach of the user. In some embodiments, the flowable ingestible medicament is absorbable in the small intestine of the user.

In some embodiments, the flowable ingestible medicament is suitable for treatment of one or more symptom or disease, selected from the group consisting of: Parkinsonism; Parkinson's Disease; progressive supranuclear palsy; corticobasal degeneration; multiple system atrophy; Parkinson-plus syndromes; any neurodegenerative disease in which the subject exhibits at least one, at least two, or at least three of the classical features of Parkinson's disease: tremor, postural instability, and akinesia or bradykesia; any neurodegenerative disease in which the subject positively responds to a dopaminergic treatment; any neurodegenerative disease in which the particular subject positively responds to an anticholinergic treatment; Constipation; Crohn's disease; Gastroparesis; irritable bowel syndrome (IBS); diarrhea or loose bowel movements; colitis; Hirschsprung's disease; Dyspepsia; and dysphagia.

In some embodiments, the flowable ingestible medicament includes or includes an ingestible medicament selected from the group consisting of: Levodopa; at least one dopaminergic agent; at least one catecholamine precursor; a dopamine precursor; at least one dopamine precursor agent; (L)-3,4-dihydroxyphenylalanine; N-methyl-N-(2-propynyl)-2-methyl-1-phenylethyl-2-amine; tyrosine hydroxylase; apomorphine; at least one anticholinergic agent; at least one agent selected to antagonize at least one cholinergic receptor; benzhexol; orphenadrine; at least one selective allosteric potentiator of metabotropic glutamate receptor 4 (mGluR4); N-phenyl-7-(hydroxylimino)cyclopropa[b]chromen-1a-carboxamide; at least one osmotic agent; magnesium citrate; magnesium hydroxide; polyethylene glycol; sodium phosphate; MiraLAX®; at least one contraction stimulating agent; bisacodyl; senna; Correctol; Ducodyl; Dulcolax; Senexon; Senokot; at least one stool softening agent; docusate sodium; Colace; Linaclotide; Lactulose; Lubiprostone; Plecanatide; Prucaltride; Loperamide; and bismuth subsalicylate.

In accordance with a further embodiment of the present invention, there is provided a vibrating ingestible capsule adapted to be attached to a medicament delivery compartment for delivering a flowable ingestible medicament disposed within the medicament delivery compartment into the gastrointestinal tract of a user, the vibrating ingestible capsule including:
  a housing including an attachment mechanism adapted for mutual attachment to a corresponding attachment mechanism of the medicament delivery compartment;
  a vibrating agitator disposed within the housing and adapted such that, in a vibration mode of operation, the housing exerts vibrations on an environment surrounding the vibrating ingestible capsule;
  a power supply disposed within the housing and adapted to power the vibrating agitator; and
  a control element adapted to activate the vibrating agitator to be operative in the vibration mode of operation, wherein at least one vibration parameter of the vibrating agitator is set so as to promote at least one of delivery of the flowable ingestible medicament from the medicament delivery compartment into an environment surrounding the medicament delivery compartment and absorption of the flowable ingestible medicament into the bloodstream of the user.

In some embodiments, the at least one vibration parameter includes at least one of a vibration frequency, a cumulative vibration duration, a number of vibration cycles per time unit, a duration of a vibration duration within a vibration cycle, a duration of a repose duration within a vibration cycle, a total duration of a single vibration cycle, and a net force exerted by the housing on the environment.

In some embodiments, the control element is adapted to control a timing or activation delay of the vibration mode of operation such that the vibration mode of operation at least partially transpires within a region of the gastrointestinal tract in which the flowable ingestible medicament is absorbable by the body of the user.

In some embodiments, the control element is adapted to control a timing or activation delay of the vibration mode of operation such that the vibration mode of operation at least partially transpires within at least one of an estimated absorption time period and an actual absorption time period of the flowable ingestible medicament within the gastrointestinal tract of the user.

In some embodiments, the control element is adapted to activate the vibrating agitator to be operative in the vibration mode of operation in response to receipt of an activation input.

In some embodiments, the vibrating ingestible capsule further includes at least one sensor adapted to provide the activation input to the control element.

In some embodiments, the at least one sensor includes an illumination sensor, adapted to provide an input indicating transition of the vibrating ingestible capsule from an illuminated environment to a dark environment.

In some embodiments, the at least one sensor includes a pressure sensor, adapted to provide an input indicating pressure applied to the vibrating ingestible capsule, which pressure is indicative of the vibrating ingestible capsule moving through a pharynx of the user.

In some embodiments, the at least one sensor includes a temperature sensor, adapted to provide an input indicating transition of the vibrating ingestible capsule from an area with ambient temperature to an area with a human body temperature.

In some embodiments, the at least one sensor includes an accelerometer, adapted to provide an input in response to a detected activation motion carried out with the vibrating ingestible capsule.

In some embodiments, the at least one sensor includes a moisture sensor, adapted to provide an input indicating transition of the vibrating ingestible capsule from a dry environment to a humid environment.

In some embodiments, the vibrating ingestible capsule is functionally associated with a control unit remote from the vibrating ingestible capsule, and wherein the control element is adapted to receive the activation input from the control unit.

In some embodiments, the control element is adapted to receive the activation input following ingesting of the vibrating ingestible capsule.

In some embodiments, the control element is adapted to receive the activation input prior to ingesting of the vibrating ingestible capsule.

In some embodiments, the control element is adapted to receive the activation input by receiving a vibration protocol to be used by the control element to control operation of the vibrating agitator.

In some embodiments, the vibrating agitator includes at least a radial agitation mechanism adapted, in the vibration mode of operation, to exert radial forces on the housing, in a radial direction with respect to a or the longitudinal axis of the housing, thereby to cause the vibrations exerted by the housing.

In some embodiments, the vibrating agitator includes at least an axial agitation mechanism adapted, in the vibration mode of operation, to exert axial forces on the housing, in an axial direction with respect to a or the longitudinal axis of the housing, thereby to cause the vibrations exerted by the housing.

In some embodiments, the vibrating agitator includes a radial agitation mechanism adapted, in the vibration mode of operation, to exert radial forces on the housing, in a radial direction with respect to a or the longitudinal axis of the housing, and a separate axial agitation mechanism adapted, in the vibration mode of operation, to exert axial forces on the housing, in an axial direction with respect to a or the longitudinal axis of the housing.

In some embodiments, the vibrating agitator includes a single agitation mechanism adapted, in the vibration mode of operation, to exert radial forces on the housing in a radial direction with respect to a or the longitudinal axis of the housing, and to exert axial forces on the housing, in an axial direction with respect to the longitudinal axis of the housing.

In some embodiments, the control element is adapted to control the vibrating agitator such that the vibrating mode of operation includes a plurality of cycles, each of the cycles including a vibration duration followed by a repose duration, wherein the housing exerts the vibrations during the vibration duration. In some embodiments, the repose duration is greater than the vibration duration.

In some embodiments, the vibration duration is in the range of 0.1 second to 10 seconds, 1 second to 10 seconds, 1 second to 9 seconds, 2 seconds to 9 seconds, 3 seconds to 9 seconds, 3 seconds to 8 seconds, 3 seconds to 7 seconds, 3 seconds to 6 seconds, 4 seconds to 6 seconds, or 5 seconds to 6 seconds.

In some embodiments, the repose duration is in the range of 1 second to 180 seconds, 3 seconds to 180 seconds, 5 seconds to 180 seconds, 5 seconds to 150 seconds, 5 seconds to 120 seconds, 8 seconds to 100 seconds, 8 seconds to 30 seconds, 10 seconds to 80 seconds, 10 seconds to 70 seconds, 10 seconds to 60 seconds, 10 seconds to 50 seconds, 10 seconds to 40 seconds, 10 seconds to 30 seconds, 10 seconds to 20 seconds, or 15 seconds to 20 seconds.

In some embodiments, a duration of each of the plurality of cycles is in the range of 1.1 seconds to 200 seconds, 5 seconds to 200 seconds, 10 seconds to 200 seconds, 10 seconds to 150 seconds, 10 seconds to 100 seconds, 10 seconds to 80 seconds, 10 seconds to 50 seconds, 10 seconds to 40 seconds, 10 seconds to 30 seconds, 15 seconds to 50 seconds, 15 seconds to 40 seconds, 15 seconds to 30 seconds, or 15 seconds to 25 seconds.

In some embodiments, the control element is adapted to control the vibrating agitator such that a cumulative duration of the vibrating mode of operation is in the range of 1 hour to 12 hours, 2 hours to 10 hours, 2 hours to 8 hours, 2 hours to 6 hours, 2 hours to 4 hours, or 2 hours to 3 hours.

In some embodiments, the vibrating agitator is configured to exert forces on the housing of the vibrating ingestible capsule, such that a net force exerted by the housing on the environment thereof is in the range of 50 grams force (gf) to 600 gf, 50 gf to 550 gf, 100 gf to 550 gf, 100 gf to 500 gf, 150 gf to 500 gf, 200 gf to 500 gf, or 200 gf to 450 gf.

In some embodiments, the vibrating agitator is configured to exert the forces on the housing to attain a housing vibrational frequency within a range of 10 Hz to 650 Hz, 15 Hz to 600 Hz, 20 Hz to 550 Hz, 30 Hz to 550 Hz, 50 Hz to 500 Hz, 70 Hz to 500 Hz, 100 Hz to 500 Hz, 130 Hz to 500 Hz, or 150 Hz to 500 Hz.

In some embodiments, the housing is adapted to be fixedly attached to a second housing of the medicament delivery compartment. In some embodiments, the housing is adapted to be attached to the medicament delivery compartment by snap fit engagement. In some embodiments, the housing is adapted to be attached to the medicament delivery compartment by threaded engagement. In some embodiments, the housing is adapted to be attached to the medicament delivery compartment by adhering. In some embodiments, the housing is adapted to be attached to the medicament delivery compartment by soldering.

In accordance with another further embodiment of the present invention, there is provided a method for delivering a flowable ingestible medicament into the gastrointestinal tract of a user, the method including:
providing an ingestible device including:
a housing including a first housing portion and a second housing portion, the second housing portion having a portal formed therein;
a vibrating agitator disposed within the housing and adapted such that, in a vibration mode of operation, the housing exerts vibrations on an environment surrounding the ingestible device;
a power supply disposed within the housing and adapted to power the vibrating agitator; and
a control element adapted to activate the vibrating agitator to be operative in the vibration mode of operation;
a flexible and collapsible medicament reservoir having the flowable ingestible medicament disposed therein;
a reservoir biasing mechanism applying pressure to the flexible and collapsible medicament reservoir;
a conduit extending from the medicament reservoir to the portal, and sealing the portal; and
a valve including a weight and a valve biasing mechanism adapted, in a closed operative orientation, to bias the weight against the conduit so as to block flow through the conduit, and in an open operative orientation to remove the weight from the conduit so as to allow fluid to flow through the conduit, the valve being functionally associated with at least one of the housing and the vibrating agitator,
ingesting the ingestible device by the user; and
following the user ingesting the device, controlling the vibrating agitator such that in the vibration mode of operation, at least some of the vibrations exerted by the vibrating agitator or by the housing are applied to the valve biasing mechanism and periodically transition the valve between the closed operative orientation and the open operative orientation,
wherein, during the controlling, when the vibrating agitator is in the vibration mode of operation and the valve is in the open operative orientation, pressure applied by the reservoir biasing mechanism to the reservoir causes the flowable ingestible medicament to flow from the reservoir, via the conduit and the portal, to an environment surrounding the assembly.

In some embodiments, providing includes providing the ingestible device wherein the first housing portion and the second housing portion include a single housing including the portal and defining a single hollow, the single hollow having disposed therein the vibrating agitator, the power supply, the control element, the flexible and collapsible medicament reservoir, the reservoir biasing mechanism, and the conduit.

In some embodiments, the weight includes the vibrating agitator.

In accordance with yet another embodiment of the present invention, there is provided a method for delivering a flowable ingestible medicament into the gastrointestinal tract of a user, the method including:
providing a vibrating ingestible capsule including:
a housing;
a vibrating agitator disposed within the housing and adapted such that, in a vibration mode of operation, the housing exerts vibrations on an environment surrounding the vibrating ingestible capsule;
a power supply disposed within the housing and adapted to power the vibrating agitator; and
a control element adapted to activate the vibrating agitator to be operative in the vibration mode of operation; and
forming an ingestible device by attaching to the vibrating ingestible capsule a medicament delivery compartment, the medicament delivery compartment including:
a second housing portion having a portal formed therein;
a flexible and collapsible medicament reservoir having the flowable ingestible medicament disposed therein;
a reservoir biasing mechanism applying pressure to the flexible and collapsible medicament reservoir;
a conduit extending from the medicament reservoir to the portal, and sealing the portal; and
a valve including a weight and valve biasing mechanism adapted, in a closed operative orientation, to bias the weight against the conduit so as to block flow through the conduit, and in an open operative orientation to remove the weight from the conduit so as to allow fluid to flow through the conduit, the valve being functionally associated with at least one of the housing and the vibrating agitator;
ingesting the ingestible device by the user; and
following the user ingesting the device, controlling the vibrating ingestible capsule such that in the vibration mode of operation, at least some of the vibrations exerted by the vibrating agitator or by the housing are applied to the valve biasing mechanism and periodically transition the valve between the closed operative orientation and the open operative orientation,
wherein, during the controlling, when the vibrating agitator is in the vibration mode of operation and the valve is in the open operative orientation, pressure applied by the reservoir biasing mechanism to the reservoir causes the flowable ingestible medicament to flow from the reservoir, via the conduit and the portal, to an environment surrounding the device.

In some embodiments, the method further includes, prior to the attaching, filling the medicament reservoir with the flowable ingestible medicament.

In some embodiments, controlling the vibrating ingestible capsule includes setting at least one vibration parameter of the vibrating ingestible capsule so as to promote transitioning of the valve between the closed operative orientation and the open operative orientation.

In some embodiments, controlling the vibrating ingestible capsule includes setting at least one vibration parameter of the vibrating ingestible capsule so as to promote absorption of the ingestible medicament into the bloodstream of the user.

In some embodiments, setting the at least one vibration parameter includes setting at least one of a vibration frequency, a cumulative vibration duration, a number of vibration cycles per time unit, a duration of a vibration duration within a vibration cycle, a duration of a repose duration within a vibration cycle, a total duration of a single vibration cycle, and a net force exerted by the housing on the environment.

In some embodiments, the housing of the vibrating ingestible capsule includes an attachment mechanism, the second housing portion includes a corresponding attachment mechanism, and the attaching includes mutually attaching the housing of the vibrating ingestible capsule to the second housing portion.

In some embodiments, the attaching includes fixedly attaching the second housing portion to the vibrating ingestible capsule. In some embodiments, the attaching includes attaching the second housing portion to the vibrating ingestible capsule by snap fit engagement. In some embodiments, the attaching includes attaching the second housing portion to the vibrating ingestible capsule by threaded engagement. In some embodiments, the attaching includes attaching the second housing portion to the vibrating ingestible capsule by adhering. In some embodiments, the attaching includes attaching the second housing portion to the vibrating ingestible capsule by soldering.

In some embodiments, the controlling includes controlling a timing or activation delay of the vibration mode of operation such that the vibration mode of operation at least partially transpires within a region of the gastrointestinal tract in which the flowable ingestible medicament is absorbable by the body of the user.

In some embodiments, the controlling includes controlling a timing or activation delay of the vibration mode of operation such that the vibration mode of operation at least partially transpires within at least one of an estimated absorption time period and an actual absorption time period of the flowable ingestible medicament released from reservoir within the gastrointestinal tract of the user.

In some embodiments, the method further includes, prior to the controlling, at the control element receiving an activation input, and the controlling includes activating the vibrating agitator to be operative in the vibration mode of operation following the receiving the activation input.

In some embodiments, the receiving the activation input includes receiving the activation input from at least one sensor.

In some embodiments, the receiving the activation input includes receiving, from an illumination sensor, an input indicating transition of the assembly from an illuminated environment to a dark environment.

In some embodiments, the receiving the activation input includes receiving, from a pressure sensor, an input indicating pressure applied to the assembly, which pressure is indicative of the assembly moving through a pharynx of the user.

In some embodiments, the receiving the activation input includes receiving, from a temperature sensor, an input indicating transition of the assembly from an area with ambient temperature to an area with a human body temperature.

In some embodiments, the receiving the activation input includes receiving, from an accelerometer, an input in response to a detected activation motion carried out with the assembly.

In some embodiments, the receiving the activation input includes receiving, from a moisture sensor, an input indicating transition of the assembly from a dry environment to a humid environment.

In some embodiments, the receiving the activation input includes receiving the activation input from a control unit remote from the assembly and functionally associated with the control element.

In some embodiments, the receiving the activation input occurs following the ingesting of the assembly.

In some embodiments, the receiving the activation input occurs prior to the ingesting of the assembly.

In some embodiments, the receiving the activation input includes receiving a vibration protocol to be used by the control element for the controlling operation of the vibrating agitator.

In some embodiments, the controlling the vibrating agitator includes controlling the vibrating agitator such that the vibrating mode of operation includes a plurality of cycles, each of the cycles including a vibration duration followed by a repose duration, wherein the housing exerts the vibrations during the vibration duration. In some embodiments, the repose duration is greater than the vibration duration.

In some embodiments, the vibration duration is in the range of 0.1 second to 10 seconds, 1 second to 10 seconds, 1 second to 9 seconds, 2 seconds to 9 seconds, 3 seconds to 9 seconds, 3 seconds to 8 seconds, 3 seconds to 7 seconds, 3 seconds to 6 seconds, 4 seconds to 6 seconds, or 5 seconds to 6 seconds.

In some embodiments, the repose duration is in the range of 1 second to 180 seconds, 3 seconds to 180 seconds, 5 seconds to 180 seconds, 5 seconds to 150 seconds, 5 seconds to 120 seconds, 8 seconds to 100 seconds, 8 seconds to 30 seconds, 10 seconds to 80 seconds, 10 seconds to 70 seconds, 10 seconds to 60 seconds, 10 seconds to 50 seconds, 10 seconds to 40 seconds, 10 seconds to 30 seconds, 10 seconds to 20 seconds, or 15 seconds to 20 seconds.

In some embodiments, a duration of each of the plurality of cycles is in the range of 1.1 seconds to 200 seconds, 5 seconds to 200 seconds, 10 seconds to 200 seconds, 10 seconds to 150 seconds, 10 seconds to 100 seconds, 10 seconds to 80 seconds, 10 seconds to 50 seconds, 10 seconds to 40 seconds, 10 seconds to 30 seconds, 15 seconds to 50 seconds, 15 seconds to 40 seconds, 15 seconds to 30 seconds, or 15 seconds to 25 seconds.

In some embodiments, the controlling includes controlling the vibrating agitator such that a cumulative duration of the vibrating mode of operation is in the range of 1 hour to 12 hours, 2 hours to 10 hours, 2 hours to 8 hours, 2 hours to 6 hours, 2 hours to 4 hours, or 2 hours to 3 hours.

In some embodiments, the controlling including controlling the vibrating agitator to exert forces on the housing of the vibrating ingestible capsule, such that a net force exerted by the housing on the environment thereof is in the range of 50 grams force (gf) to 600 gf, 50 gf to 550 gf, 100 gf to 550 gf, 100 gf to 500 gf, 150 gf to 500 gf, 200 gf to 500 gf, or 200 gf to 450 gf.

In some embodiments, the controlling including controlling the vibrating agitator to exert the forces on the housing to attain a housing vibrational frequency within a range of 10 Hz to 650 Hz, 15 Hz to 600 Hz, 20 Hz to 550 Hz, 30 Hz to 550 Hz, 50 Hz to 500 Hz, 70 Hz to 500 Hz, 100 Hz to 500 Hz, 130 Hz to 500 Hz, or 150 Hz to 500 Hz.

In some embodiments, the flowable ingestible medicament has a viscosity in the range of 100 Pa·s to 1000 Pa·s.

In some embodiments, the flowable ingestible medicament is absorbable in the stomach of the user. In some embodiments, the flowable ingestible medicament is absorbable in the small intestine of the user.

In some embodiments, the flowable ingestible medicament is suitable for treatment of one or more symptom or disease, selected from the group consisting of:

Parkinsonism; Parkinson's Disease; progressive supranuclear palsy; corticobasal degeneration; multiple system atrophy; Parkinson-plus syndromes; any neurodegenerative disease in which the subject exhibits at least one, at least two, or at least three of the classical features of Parkinson's disease: tremor, postural instability, and akinesia or bradykesia; any neurodegenerative disease in which the subject positively responds to a dopaminergic treatment; any neurodegenerative disease in which the particular subject positively responds to an anticholinergic treatment; Constipation; Crohn's disease; Gastroparesis; irritable bowel syndrome (IBS); diarrhea or loose bowel movements; colitis; Hirschsprung's disease; Dyspepsia; and dysphagia.

In some embodiments, the flowable ingestible medicament includes or includes an ingestible medicament selected from the group consisting of:

Levodopa; at least one dopaminergic agent; at least one catecholamine precursor; a dopamine precursor; at least one dopamine precursor agent; (L)-3,4-dihydroxyphenylalanine; N-methyl-N-(2-propynyl)-2-methyl-1-phenylethyl-2-amine; tyrosine hydroxylase; apomorphine; at least one anticholinergic agent; at least one agent selected to antagonize at least one cholinergic receptor; benzhexol; orphenadrine; at least one selective allosteric potentiator of metabotropic glutamate receptor 4 (mGluR4); N-phenyl-7-(hydroxylimino)cyclopropa[b]chromen-1a-carboxamide; at least one osmotic agent; magnesium citrate; magnesium hydroxide; polyethylene glycol; sodium phosphate; MiraLAX®; at least one contraction stimulating agent; bisacodyl; senna; Correctol; Ducodyl; Dulcolax; Senexon; Senokot; at least one stool softening agent; docusate sodium; Colace; Linaclotide; Lactulose; Lubiprostone; Plecanatide; Prucaltride; Loperamide; and bismuth subsalicylate.

BRIEF DESCRIPTION OF THE FIGURES

The foregoing discussion will be understood more readily from the following detailed description of the invention, when taken in conjunction with the accompanying FIGS. 1-7), in which:

FIGS. 4A and 4B are partial planar sectional illustrations of the device of FIG. 2, where the medicament reservoir is full, and the valve is in closed and open operative orientations, respectively;

FIG. 5 is a partial planar sectional illustrations of the device of FIG. 2, where the medicament reservoir is empty, and the valve is in a closed operative orientation;

FIG. 7 is a schematic flowchart of a method for delivering a flowable ingestible medicament into the gastrointestinal tract of user according to the present invention, the method being based on use of any one of the devices of FIGS. 1 to 6.

DESCRIPTION OF THE PREFERRED EMBODIMENTS

Figure 1:
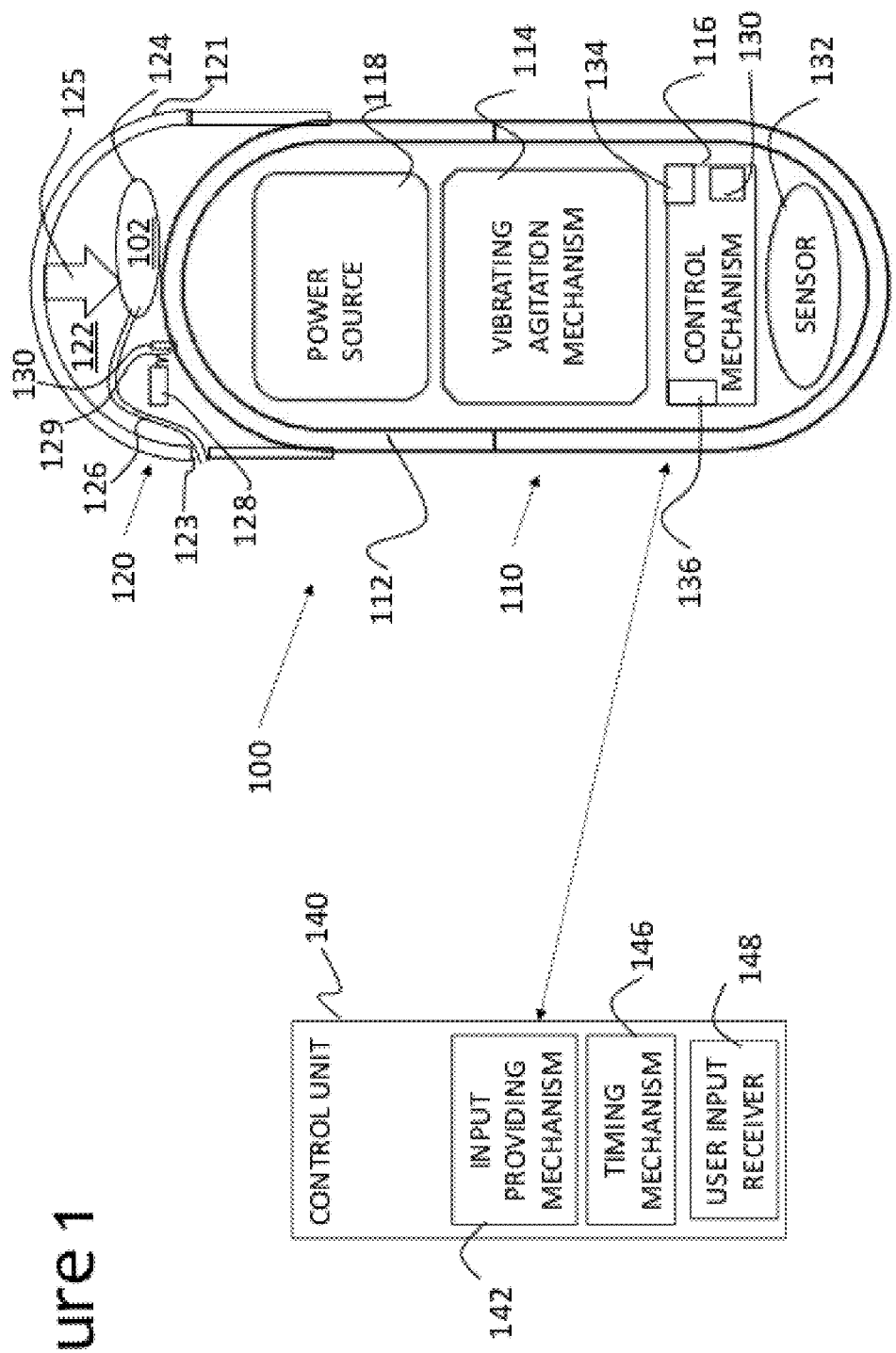
FIG. 1 is a schematic block diagram of a device for delivering a flowable ingestible medicament into the gastrointestinal tract of a user according to an embodiment of the present invention.

The principles of the inventive devices and methods for delivery of an ingestible medicament into the body of a user, and specifically to devices and methods for such delivery of an ingestible medicament which include a vibrating capsule, may be better understood with reference to the drawings and the accompanying description.

Before explaining at least one embodiment of the invention in detail, it is to be understood that the invention is not limited in its application to the details of construction and the arrangement of the components set forth in the following description or illustrated in the drawings. The invention is capable of other embodiments or of being practiced or carried out in various ways. Also, it is to be understood that the phraseology and terminology employed herein is for the purpose of description and should not be regarded as limiting.

For the purposes of this application, the term "user" relates to a human.

For the purposes of this application, the term "vibrating ingestible capsule" relates to an ingestible capsule adapted to at least intermittently vibrate, for a cumulative duration of at least one minute, in accordance with a vibration protocol of the capsule.

For the purposes of this application, the term "vibrating agitator" refers to any type of mechanism that vibrates or causes elements in its vicinity to vibrate, including a motor drive agitator such as a motor drive eccentric weight or a motor drive pendulum.

For the purposes of this application, the term "intermittently activated vibrating agitator" refers to a vibrating agitator that vibrates or causes elements in its vicinity to vibrate and is operative at certain times, and does not vibrate or cause elements in its vicinity to vibrate at other times, the activation times being selected by a control element or other control unit controlling the vibrating agitator.

For the purposes of this application, the term "control element", and the equivalent term "controller" refer to a component for controlling operation of mechanical and/or electrical components of the capsule, which includes a processing unit functionally associated with a non-tangible computer readable storage medium. The storage medium stores instructions, which, when executed by the processing unit, cause the processing unit to carry out actions which control the operation of the mechanical and/or electrical components of the capsule. For example, the instructions may include instructions to activate operation of a vibrating agitator at a specific time, frequency, cycle, and/or for a specific duration. The control element may be functionally associated with, or may include, a transceiver for receiving input, which input may be used to trigger execution of specific instructions stored in the storage medium.

For the purposes of this application, the term "biasing mechanism" refers to any structure, or device, adapted to apply pressure to a second element, even when the position of the second element changes relative to an anchoring point of the structure or device. Biasing mechanisms include springs, such as compression springs and extension springs, as well as spring loaded leaves, plungers, and the like.

For the purposes of this application, the term "vibration protocol" relates to a protocol specifying vibration parameters of an intermittently activated vibrating agitator of a vibrating ingestible capsule. Typically, the vibration protocol relates to an activation delay for initiating vibration (e.g., a duration between "initial" activation of the capsule and the first activation of the vibrating agitator), a vibration rate (number of vibration cycles per hour), a vibration duration and a repose duration for each vibration cycle, a vibration frequency, an amount of force exerted by the vibrations, and the like.

For the purposes of this application, the term "treatment procedure" relates to parameters of a treatment utilizing vibrating ingestible capsules, which are typically defined by a treating physician or medical practitioner. For example, the treatment procedure may include the number of capsules to be taken within a specific time duration (e.g., 3 capsules per week, 2 capsules per day), the frequency at which capsules should be taken, the time of day at which capsules should be taken, whether the capsule should be taken with or without food, and the like.

For the purpose of this application, the term "treatment protocol" relates to all aspects of treatment of a user with a vibrating ingestible capsule, and includes the treatment procedure as well as the vibration protocol to be used for treating the user.

For the purpose of this application, the term "activation input" relates to an input received by a control element or control element of a vibrating ingestible capsule, which causes the control element or control element of the capsule to activate itself, so as to be able to process inputs and/or to control additional components of the capsule. The activation input may be received from an element forming part of the capsule, such as a sensor sensing specific conditions in which the capsule should be activated, or from a remote source, such as a remote control element, for example by way of a signal transmitted to the capsule, magnetic field applied to the capsule, specific motion applied to the capsule, or any other type of input provided to the capsule from a remote source.

For the purpose of this application, a vibrating ingestible capsule is said to be in an "inoperative state" when the capsule is in a storage condition, intended to preserve the life of a battery thereof. In the inoperative state, components of the capsule which are intended to receive or to provide an activation input, such as specific sensors, transceivers, and/or timing mechanisms may be active at least to a minimal degree. However, in the inoperative state, no vibration takes place, and a control element controlling vibration of the capsule is inactive.

For the purpose of this application, a vibrating ingestible capsule is said to be in an "operative state" when the control element of the capsule is processing inputs and data, and can cause a vibrating agitator of the capsule to vibrate or cause elements in its vicinity to vibrate.

For the purpose of this application, an "ingestible medicament" is at least partially absorbable to the bloodstream from within the stomach, small intestine, and large intestine, and more typically, within the stomach or small intestine.

For the purpose of this application, the term "partially absorbable" is meant to include the possibility that the environment within the gastrointestinal tract (including acids, enzymes, etc. thereof) may chemically modify the ingested medicament in order to achieve the characteristic "partially absorbable".

For the purposes of this application the term "flowable ingestible medicament" relates to any dosage form of an ingestible medicament which can flow through a conduit, such as a liquid ingestible medicament, a suspension of an ingestible medicament, a gaseous ingestible medicament, a solution of an ingestible medicament, a dissolved ingestible medicament, a melted ingestible medicament, and the like.

For the purposes of this application, the disclosure of a commercial name of a material or drug is meant to be a disclosure of the corresponding generic material or drug, and of the active ingredient(s) within the commercial material or drug and/or within the corresponding generic material or drug.

For the purpose of this application, an estimated absorption time may be determined as follows:
(i) ingestible medicaments that are absorbed in the stomach have an estimated absorption time within a range of 0.5 to 1.5 hours from the time of ingestion of the ingestible medicament;
(ii) ingestible medicaments that are absorbed in the small intestine have an estimated absorption time within a range of 1.0 to 5 hours from the time of ingestion of the ingestible medicament;
(iii) ingestible medicaments that are absorbed in both the stomach and the small intestine have an estimated absorption time within a range of 0.5 to 5 hours from the time of ingestion of the ingestible medicament;
(iv) ingestible medicaments that are absorbed in the large intestine have an estimated absorption time of at least 4 hours, and more typically, within a range of 4 to 30 hours, 6 to 30 hours, 6 to 20 hours, or 8 to 20 hours from the time of ingestion of the ingestible medicament.

The location within the GI tract at which the particular ingestible medicament is absorbed to the bloodstream may often be public knowledge. This location may be provided by, or known to, the manufacturer and/or distributor of the particular ingestible medicament. Alternatively or additionally, the location may be known to relevant medical practitioners, including doctors and pharmacists, and more particularly, to a medical practitioner of the user.

For the purpose of this application, an actual absorption time may be determined from clinical data, in vivo or in vitro, according to accepted clinical procedures known to those of skill in the art. Since actual absorption is achieved over a period of time, the "actual absorption time" or "actual absorption time period" may be defined by the time period at which between 20% and 80% of the absorption occurs. In the absence of such data, the "actual absorption time" or "actual absorption time period" may be defined by determining the "peak" actual absorption time, and building a time period of up to 1 hour on each side of the peak time.

For the purpose of this application, a recovery time of a resilient conduit relates to the duration from a time from release of a force pinching the resilient conduit such that no fluid can flow therethrough, till the conduit is not blocking the flow. This may occur when the conduit is partially recovered, i.e. the force has been removed such that there is a hollow in the conduit but the conduit has not returned to its initial diameter, or when the conduit is fully recovered and has returned to its initial, nominal diameter.

For the purpose of this application, the term "Parkinsonism" is meant to include Parkinson's disease, or symptoms of neurodegeneration associated therewith.

For the purpose of this application, the term "Parkinsonism" is meant to include progressive supranuclear palsy, or symptoms of neurodegeneration associated therewith.

For the purpose of this application, the term "Parkinsonism" is meant to include corticobasal degeneration, or symptoms of neurodegeneration associated therewith.

For the purpose of this application, the term "Parkinsonism" is meant to include multiple system atrophy, or symptoms of neurodegeneration associated therewith.

For the purpose of this application, the term "Parkinsonism" is meant to include Parkinson-plus syndromes (also known as disorders of multiple system degeneration), or symptoms of neurodegeneration associated therewith.

For the purpose of this application, the term "Parkinsonism" is meant to include any neurodegenerative disease in which the subject exhibits at least one (and typically at least two or three) of the classical features of Parkinson's disease: tremor, postural instability, and akinesia or bradykesia.

For the purpose of this application, the term "Parkinsonism" is meant to include any neurodegenerative disease in which the subject positively responds to a dopaminergic treatment.

For the purpose of this application, the term "Parkinsonism" is meant to include any neurodegenerative disease in which the particular subject positively responds to an anticholinergic treatment.

For the purpose of this application, the term "Parkinsonism" is meant to include any neurodegenerative disease in which a dopaminergic treatment is clinically utilized to treat the sufferers or subjects.

For the purpose of this application, the term "Parkinsonism" is meant to include any neurodegenerative disease in which an anticholinergic treatment is clinically utilized to treat the sufferers or subjects.

For the purpose of this application, the term "Parkinson's disease" (PD) is meant as used by those of skill in the art of neurodegenerative diseases. It is believed that PD is due to the loss of brain cells that produce dopamine. Early signs and symptoms of Parkinson's disease include at least one of tremors (or trembling), slowness of movement, body rigidity and stiffness, and gait problems.

For the purpose of this application, the term "treatment of Parkinsonism" and the like refers to at least one of: (i) delaying onset of Parkinsonism (e.g., PD); (ii) mitigating the development of Parkinsonism (e.g., PD); and (iii) managing a condition of Parkinsonism (e.g., PD).

For the purpose of this application, the term "ailment of the GI tract" is meant to include chronic or acute constipation, or symptoms associated therewith.

For the purpose of this application, the term "ailment of the GI tract" is meant to include gastroparesis, or symptoms associated therewith.

For the purpose of this application, the term "ailment of the GI tract" is meant to include Crohn's disease, or symptoms associated therewith.

For the purpose of this application, the term "ailment of the GI tract" is meant to include chronic or acute diarrhea, or symptoms associated therewith.

For the purpose of this application, the term "ailment of the GI tract" is meant to include colitis, or symptoms associated therewith.

For the purpose of this application, the term "ailment of the GI tract" is meant to include dyspepsia or dysphagia, or symptoms associated therewith.

For the purpose of this application, the term "ailment of the GI tract" is meant to include Hirschsprung's disease, or symptoms associated therewith.

For the purpose of this application, the term "ailment of the GI tract" is meant to include irritable bowel syndrome, or symptoms associated therewith.

For the purpose of this application, the term "ailment of the GI tract" is meant to include any disease in which the subject positively responds to an osmotic gastrointestinal treatment.

For the purpose of this application, the term "ailment of the GI tract" is meant to include any disease in which the particular subject positively responds to a stool softening treatment.

For the purpose of this application, the term "ailment of the GI tract" is meant to include any disease in which the particular subject positively responds to a GI contraction inducing treatment.

For the purpose of this application, the term "ailment of the GI tract" is meant to include any disease in which the subject positively responds to a GI fluid absorption inducing treatment.

For the purpose of this application, the term "managing a condition of", with respect to an ailment of the GI tract, is meant to include, inter alia, improving absorption of a medicament, such as a medicament used in the treatment of the ailment of the GI tract (e.g., Linaclotide (Linzess®)), into the bloodstream. Such condition management may be manifested by at least one of (i) improved medicament efficacy due to the increased absorption; and (ii) reduced dosage of the medicament, due to the increased medicament absorption efficacy.

For the purpose of this application, the term "managing a condition of", with respect to Parkinsonism and the like, is meant to include, inter alia, improving absorption of a medicament, such as a medicament used in the treatment of Parkinsonism (e.g., levodopa), into the bloodstream. Such condition management may be manifested by at least one of (i) improved medicament efficacy due to the increased absorption; and (ii) reduced dosage of the medicament, due to the increased medicament absorption efficacy.

Referring now to the drawings, FIG. 1 is a schematic block diagram of a device 100 for delivering a flowable ingestible medicament 102 into the gastrointestinal tract of a user according to an embodiment of the present invention.

It is a particular feature of the present invention that delivery of the flowable ingestible medicament is triggered by, and occurs only during a time at which a vibrating ingestible capsule is a vibration mode of operation, as explained in detail hereinbelow. Stated differently, delivery of the flowable ingestible medicament only occurs when the vibrating ingestible capsule is actually vibrating, and is triggered by such vibration of the vibrating ingestible capsule.

As seen in FIG. 1, device 100 includes vibrating ingestible capsule 110. Capsule 110 includes a capsule housing or shell 112, also termed a first housing portion, arranged along a longitudinal axis 113 and having disposed therein a vibrating agitator 114. A control element 116 is adapted to control operation of vibrating agitator 114, and at least one power source 118 provides power to vibrating agitator 114 and control element 116.

The vibrating ingestible capsule 110 is functionally associated with a medicament delivery compartment 120.

In some embodiments, the medicament delivery compartment 120 is distinct from the vibrating ingestible capsule 110, and is attached thereto, as illustrated in FIG. 1 and as explained hereinbelow with respect to FIG. 2. In such embodiments, the medicament delivery compartment includes a hollow medicament compartment housing 121, also termed a second housing portion, defining a hollow 122. The hollow compartment housing includes a portal 123 and is attached to housing 112 of capsule 110.

Medicament compartment housing 120 may be fixedly attached to housing 112 of vibrating ingestible capsule 110, or removable attached thereto. Medicament compartment housing 120 may be attached to housing 112 of vibrating ingestible capsule 110 using any suitable attachment method, such as by adhering, by soldering, by snap fit engagement or by threaded engagement.

In some embodiments, housing 112 of vibrating ingestible capsule 110 includes an attachment mechanism, and hollow medicament compartment housing 121 includes a corresponding attachment mechanism, for mutual attachment of vibrating ingestible capsule 110 to hollow medicament compartment housing 121. An exemplary arrangement of such attachment mechanisms is illustrated, for example, in FIGS. 3 to 4B described in detail hereinbelow.

In other embodiments, the medicament delivery compartment 120 may form part of the vibrating ingestible capsule 110, as explained hereinbelow with respect to FIG. 6. In such embodiments, the portal 123 is formed in housing 112, and the hollow of the vibrating ingestible capsule includes all components otherwise included in hollow 122, as explained hereinbelow.

A flexible and collapsible medicament reservoir 124, which is adapted to have the flowable ingestible medicament 102 disposed therein, is disposed within hollow 122, and pressure is constantly applied thereto by a reservoir biasing mechanism 125, which may be anchored to medicament compartment housing 121. A conduit 126, which may be a flexible and/or resilient conduit, extends from medicament reservoir 124 to portal 123, such that a fluid flowing through the conduit is delivered to an environment surrounding device 100. Typically, conduit 126 seals portal 123, to prevent fluid from the environment surrounding device 100 from entering the device.

A valve, which includes a weight 128 and a valve biasing mechanism 129, typically a spring, adapted, in a closed operative orientation, to block flow through the conduit 126 by biasing weight 128 against the conduit thereby to pinch the conduit, and, in an open operative orientation, to remove weight 128 from applying pressure to conduit 126, such that, following the recovery time of the conduit, fluid may flow through the conduit.

It is a particular feature of the present invention that valve biasing mechanism 129 is functionally associated with housing 112 or with vibrating agitator 114. When vibrating agitator 114 is in an inoperative state, or is operative but not in a vibration mode of operation, valve biasing mechanism 129 biases weight 128 against conduit 126, such that the valve is in the closed operative orientation and fluid cannot flow through the conduit. When vibrating agitator 114 is in a vibration mode of operation and exerts vibrations on housing 112, at least some of the exerted vibrations are applied to valve biasing mechanism 129, and cause the valve biasing mechanism to move periodically. Periodic motion of the valve biasing mechanism 129 results in corresponding periodic motion of weight 128 away from conduit 126, thereby transitioning the valve from the closed operative orientation to an open operative orientation and allowing fluid to flow through conduit 126.

Due to the flexibility and resiliency of conduit 126, when the weight 128 is moved away from the conduit, conduit 126 at least partially recovers such that fluid can flow through the conduit. Because reservoir biasing mechanism 125 constantly applies pressure to reservoir 124, upon recovery of conduit 126, enables the flowable ingestible medicament flows through the conduit, and out of portal 123, into an environment surrounding the device 100. As such, delivery of the flowable ingestible medicament is triggered by, and controlled by, vibration of the vibrating agitator 114.

The rate at which the flowable ingestible medicament is delivered into the environment surrounding device 100 is dependent on characteristics of the conduit 126, such as the diameter of the conduit, the thickness of the conduit walls, and the recovery time of the conduit, as well as on characteristics of the valve, such as the frequency of transitioning between the open and closed operative orientations of the valve.

It will be appreciated that the frequency at which valve biasing mechanism 129 transitions the valve between the open and closed operative orientations, by causing weight 128 to move towards and away from conduit 126, is dependent on the frequency of vibrations exerted by vibrating agitator 114 or by housing 112, as well as on the characteristics of the valve, such as the mass of weight 128 and the spring constant of the biasing mechanism 129.

In some embodiments, the mass of weight 128 and the length and spring constant of biasing mechanism 129 may be selected such that the valve functions as a gear reducer. In such embodiments, the frequency at which the valve transitions between the closed and open operative orientations (i.e. the frequency at which the valve biasing mechanism 129 draws weight 128 away from conduit 126 and then pushes the weight 128 back to apply pressure to conduit 126) may be smaller than the frequency of vibrations exerted by vibrating agitator 114.

In some embodiments, valve biasing mechanism 129 is anchored to housing 112. In some embodiments, valve biasing mechanism 129 may be anchored to medicament compartment housing 121, provided that the attachment between the medicament compartment housing 121 and housing 112 of vibrating ingestible capsule 110 does not dampen or reduce the frequency or intensity of vibrations applied to valve biasing mechanism 129, and that the frequency and intensity of vibrations exerted on medicament compartment housing 121 is substantially equal to that of vibrations exerted on housing 112.

Relating now to characteristics of the medicament delivery compartment 120, in some embodiments, in which the medicament delivery compartment 120 is distinct from vibrating ingestible capsule 110, hollow 122 of medicament compartment housing 121 has a volume in the range of 200 $mm^3$ to 800 $mm^3$, 300 $mm^3$ to 700 $mm^3$, or 400 $mm^3$ to 600 $mm^3$. In other embodiments, in which housing 112 houses components of medicament delivery compartment 120, the housing 112 has a volume in the range of 1000 $mm^3$ to 4000 $mm^3$.

In some embodiments, medicament reservoir 124 has a maximal volume in the range of 1 $mm^3$ to 600 $mm^3$, 1 $mm^3$ to 10 $mm^3$, 5 $mm^3$ to 20 $mm^3$, 15 $mm^3$ to 50 $mm^3$, 30 $mm^3$ to 200 $mm^3$, 100 $mm^3$ to 400 $mm^3$, or 300 $mm^3$ to 600 $mm^3$.

In some embodiments, medicament reservoir 124 has elastic or elastomeric properties, and may have a low value for Young's modulus, typically smaller than 1 GPa. In some embodiments, medicament reservoir 124 is formed of a material selected from the group consisting of: silicone rubber, natural rubber, Polyethylene, and PVC.

In some embodiments, reservoir biasing mechanism 125 includes a reservoir spring terminating in a pressure applying surface which engages an exterior surface of medicament reservoir 124, as illustrated in FIGS. 2 to 5. In such embodiments, the reservoir spring may be anchored to medicament compartment housing 121.

In some embodiments, reservoir biasing mechanism 125 has a spring constant K in the range of 1 N/m to 200 N/m.

In some embodiments, flexible and resilient conduit 126 is integrally formed with flexible and collapsible medicament reservoir 124. In other embodiments, conduit 126 is formed of a different material than medicament reservoir 124.

In order to ensure that when vibrating agitator 114 is in the vibration mode of operation, fluid can be delivered through conduit 126, the recovery time of the conduit must be sufficiently short for the conduit to recover its nominal diameter, and facilitate passage of fluid therethrough, before the conduit is once again pinched by weight 128.

As such, in some embodiments, when vibrating agitator has a frequency f, a recovery time of conduit 126 is at most equal to 1/f. In other embodiments, when valve biasing mechanism 129 has a frequency fv of transitioning the valve between the open and closed operative orientations, a recovery time of conduit 126 is at most equal to 1/fv.

In some embodiments, a recovery time of conduit 126 is at most 0.1 seconds.

In some embodiments, conduit 126 has a diameter in the range of 0.01 mm-0.9 mm.

In some embodiments, conduit 126 has a length in the range of 3 mm-25 mm.

In some embodiments, valve biasing mechanism 129 has a spring constant in the range of 0.1 N/m to 5 N/m.

In some embodiments, weight 128 has a mass in the range of 0.1 grams to 2 grams.

Relating specifically to capsule 110, power source 118 may be any suitable power source, such as one or more alkaline or silver oxide batteries, primary batteries, rechargeable batteries, capacitors and/or supercapacitors.

Intermittently activated vibrating agitator 114 is adapted to have a vibration mode of operation (also termed the first mode of operation) and a rest mode of operation (also termed the second mode of operation). In the vibration mode of operation, intermittently activated vibrating agitator 114 is adapted to exert forces on capsule housing 112, such that capsule housing 112 exerts vibrations on an environment surrounding capsule 110 and/or device 100.

In some embodiments, the capsule 110 is in an inoperative state, until the receipt of an activation input, which causes control element 116 to transition the capsule from the inoperative state to an operative state.

In some embodiments, control element 116 is functionally associated with, or includes, a timer or timing mechanism 130, such as a clock, universal clock, or stopwatch, powered by power source 118 and adapted to track at least one time characteristic, such as a duration that has passed since an activation input was received, or a duration that has passed since the user ingested capsule 110.

In some embodiments, capsule 110 is devoid of any sensors for sensing an environment thereof. In some such embodiments, control element 116 is adapted, in response to receipt of an activation input, to wait a predetermined delay time, and following the predetermined delay time, to activate vibrating agitator 114 to operate in said first vibration mode of operation.

In other embodiments, such as the embodiment illustrated in FIG. 1, capsule 110 further includes at least one sensor 132, functionally associated with control element 116. The at least one sensor 132 may be adapted to sense at least one parameter within capsule 110 or in an environment of capsule 110, and may include a temperature sensor, an illumination sensor, a moisture sensor, a pressure sensor, an accelerometer, or any other suitable sensor. In some embodiments, the at least one sensor 132 is adapted to identify a specific condition in capsule 110 or in the vicinity thereof, and to provide an activation input to control element 116 in response to identification of the condition. For example, in some embodiments the condition is indicative of the user ingesting capsule 110.

For example, in some embodiments sensor 132 may include an illumination sensor, adapted to identify transition of capsule 110 from an illuminated environment (e.g. outside the human body) to a dark environment (e.g. within the human body) and to provide an activation input in response to identification of such a transition.

As another example, in some embodiments sensor 132 may include a motion or acceleration sensor, such as an accelerometer, adapted to identify an activation motion carried out by a user on capsule 110 or on device 100 and to provide an activation input in response to identification of such a transition. An example of an accelerometer providing an activation input for a gastrointestinal capsule is provided in U.S. Pat. No. 10,314,514, which is incorporated by reference for all purposes as if fully set forth herein.

As another example, in some embodiments sensor 132 may include a pressure sensor adapted identify pressure applied to the capsule 110 or to device 100, which pressure is indicative of the capsule moving through a pharynx of the user, and to provide an activation input in response to identification of such pressure.

As a further example, in some embodiments sensor 132 may include a temperature sensor adapted to identify transition of capsule 110 or of device 100 from an area with ambient temperature (e.g. outside the human body) to an area with a human body temperature and to provide an activation input in response to identification of such a transition.

As a further example, in some embodiments sensor 132 may include a moisture sensor adapted to identify transition of capsule 110 or of device 100 from a dry area (e.g. outside the human body) to a moist area (e.g. within the human body) and to provide an activation input in response to identification of such a transition.

It will be appreciated by people of skill in the art that sensor 132 need not necessarily be disposed within capsule 110, as illustrated in FIG. 1, and may be disposed anywhere within device 100, for example within hollow 122 of medicament compartment housing 120, on an exterior of capsule 110, or on the exterior of device 100.

In some embodiments, device 100 may be functionally associated with a control unit 140, which may be remote from device 100 and from capsule 110, and which is adapted to provide one or more inputs to the capsule. In some such embodiments, capsule 110 further includes a remote input receiving mechanism 136, functionally associated with control element 116, and adapted to receive inputs from an input providing mechanism 142 of control unit 140.

In some embodiments, control unit 140 may further include a timing mechanism 146, adapted to track at least one time characteristic, such as a duration that has passed since a control instruction was provided to capsule 110.

In some embodiments, control unit 140 may further include a user input receiver 148, such as a keyboard, touch screen, or touch pad, adapted to receive input from a user, such as the user, a medical professional treating the user, or a caregiver of the user.

Control unit 140 may be any suitable type of control unit. In some embodiments, control unit may be a suitably configured smart phone or a tablet computer.

In some such embodiments, control unit 140 may provide inputs to capsule 110 by remotely transmitting the inputs from input providing mechanism 142 to remote input receiving mechanism 136, for example using a short range wireless communication method, such as radio frequency (RF) communication or Bluetooth® communication. One example of such a mechanism for providing input to a capsule is described in U.S. Pat. No. 10,478,373, which is incorporated by reference for all purposes as if fully set forth herein.

In some embodiments, control unit 140 is adapted to provide the activation input to control element 116 of capsule 110. In some such embodiments, control unit 140 provides the activation input prior to the user ingesting device 100 including capsule 110, whereas in other embodiments control unit 140 provides the activation input following ingestion of device 100 and capsule 110 by the user.

Relating to the characteristics of vibrating agitator 114, the vibrating agitator may be any suitable mechanism that can be intermittently activated and can apply suitable forces onto capsule housing 112.

In some embodiments, intermittently activated vibrating agitator 114 may include a radial agitation mechanism adapted to exert radial forces on capsule housing 112, in a radial direction with respect to the longitudinal axis of housing 112. For example, the radial agitation mechanism may include an unbalanced weight attached to a shaft of an electric motor powered by said battery, substantially as described in U.S. Pat. No. 9,707,150, which is incorporated by reference for all purposes as if fully set forth herein.

In some embodiments, intermittently activated vibrating agitator 114 may include an axial agitation mechanism adapted to exert radial forces on the capsule housing 112, in an axial direction with respect to a longitudinal axis of housing 112. For example, the axial agitation mechanism may include an electric motor powered by the battery and an urging mechanism, associated with, and driven by, the electric motor, such that the urging mechanism adapted to exert said axial forces, substantially as described in U.S. Pat. No. 9,707,150. In some embodiments, the urging mechanism adapted to exert the axial forces in opposite directions. In some embodiments, the urging mechanism is adapted to deliver at least a portion of the axial forces in a knocking mode.

In some embodiments, the forces exerted by intermittently activated vibrating agitator 114 on capsule housing 112 in the vibration mode of operation include radial forces in a radial direction with respect to the longitudinal axis of the housing and axial forces in an axial direction with respect to the longitudinal axis. In some embodiments, a single agitation mechanism exerts both the radial and the axial forces. In other embodiments, the axial forces are exerted by one agitation mechanism, and the radial forces are exerted by another, separate, agitation mechanism, where both agitation mechanisms form part of intermittently activated vibrating agitator 114.

In some embodiments, the intermittently activated vibrating agitator 114 may include a magnet mounted onto a rotor adapted to exert a magnetic field as well as radial forces on capsule housing 112. For example, such a magnetic vibrating agitator is described in U.S. Patent Application Publication No. 2016/0310357, which is incorporated by reference for all purposes as if fully set forth herein.

In some embodiments, housing 112 may include first and second members, and vibrating agitator 114 may include a mechanism adapted to effect a vibration by moving the first member of the housing in the opposite direction relative to the second member of the housing, substantially as described in U.S. Pat. No. 9,078,799, which is incorporated by reference for all purposes as if fully set forth herein.

In some embodiments, housing 112 may include a vibrating agitator 114 which makes use of a pendulum to cause vibration in the vicinity of the capsule, for example as described in CN Patent Application Number 105997466 filed on Jun. 16, 2016, which is incorporated by reference for all purposes as if fully set forth herein.

In some embodiments, or at some times, control element 116 is adapted to control vibrating agitator 114, and specifically to set at least one vibration parameter of vibrating agitator 114, so as to promote delivery of the flowable ingestible medicament into an environment surrounding device 100 and/or absorption of the ingestible medicament into the bloodstream of the user.

For example, delivery of the flowable ingestible medicament into an environment surrounding device 100 may be promoted by controlling one or more characteristics of the vibrating agitator 114 such that conduit 126 is open for relatively long durations, facilitating rapid delivery of the flowable medicament into the gastrointestinal tract.

As another example, absorption of the ingestible medicament may be promoted by the vibration promoting emulsification of the ingestible medicament. As yet another example, absorption of the ingestible medicament may be promoted by the vibration causing a hydrophobic phase of the ingestible medicament to form smaller bubbles, thereby increasing the surface area of the hydrophobic phase for absorption thereof. In another example, absorption of the ingestible medicament may be promoted by the vibration causing greater exposure of the ingestible medicament to the environment.

In some embodiments, or at some times, control element 116 may be adapted to control vibrating agitator 114 so that the capsule applies forces to an environment thereof, such that within the gastrointestinal tract, a mechanical stimulation of the wall of the gastrointestinal tract is effected.

In some such embodiments, the at least one vibration parameter includes at least one of a vibration frequency, a cumulative vibration duration, a number of vibration cycles per time unit, a duration of a vibration duration within a vibration cycle, a duration of a repose duration within a vibration cycle, a total duration of a single vibration cycle, and a net force exerted by said housing on said environment, as explained in further detail hereinbelow.

In some embodiments, control element 116 is adapted to control a timing or activation delay of the vibration mode of operation of the vibrating agitator 114 such that the vibration mode of operation at least partially transpires within a region of the gastrointestinal tract in which the flowable ingestible medicament is absorbable by the body of the user, and at which it is desirable for the flowable ingestible medicament to be delivered into the gastrointestinal tract.

In some embodiments, control element 116 is adapted to control a timing or activation delay of the vibration mode of operation of the vibrating agitator 114 such that the vibration mode of operation at least partially transpires within an estimated absorption time period of the flowable ingestible medicament 102 within the gastrointestinal tract of the user.

In some embodiments, control element 116 is adapted to control a timing or activation delay of the vibration mode of operation of the vibrating agitator 114 such that the vibration mode of operation at least partially transpires within an actual absorption time period of the flowable ingestible medicament 102 within the gastrointestinal tract of the user.

In the vibrating mode of operation, intermittently activated vibrating agitator 114 is adapted to have a plurality of vibration cycles, where each cycle includes a vibration duration followed by a repose duration. Forces are exerted by the vibrating agitator 114 on capsule housing 112 only during the vibration duration, and as such, capsule housing 112 only exerts forces on an environment thereof during the vibration duration.

In some embodiments, the number of vibration cycles per hour is in the range of 20 to 400, 40 to 400, 60 to 400, 80 to 400, 40 to 380, 60 to 380, 80 to 380, 40 to 360, 60 to 360, 80 to 360, 100 to 360, 100 to 330, 100 to 300, 100 to 280, 100 to 250, 100 to 220, 100 to 200, 120 to 300, 120 to 280, 120 to 250, 120 to 220, 120 to 200, 150 to 300, 150 to 280, 150 to 250, 150 to 220, 150 to 200, 170 to 300, 170 to 250, 170 to 220, or 170 to 200.

In some embodiments, the repose duration is greater than the vibration duration.

In some embodiments, the vibration duration is in the range of 0.1 second to 10 seconds, 1 second to 10 seconds, 1 second to 9 seconds, 2 seconds to 9 seconds, 3 seconds to 9 seconds, 3 seconds to 8 seconds, 3 seconds to 7 seconds, 3 seconds to 6 seconds, 4 seconds to 6 seconds, or 5 seconds to 6 seconds.

In some embodiments, the repose duration is in the range of 1 second to 180 seconds, 3 seconds to 180 seconds, 5 seconds to 180 seconds, 5 seconds to 150 seconds, 5 seconds to 120 seconds, 8 seconds to 100 seconds, 8 seconds to 30 seconds, 10 seconds to 80 seconds, 10 seconds to 70 seconds, 10 seconds to 60 seconds, 10 seconds to 50 seconds, 10 seconds to 40 seconds, 10 seconds to 30 seconds, 10 seconds to 20 seconds, or 15 seconds to 20 seconds.

In some embodiments, the total duration of one vibration cycle is in the range of 1.1 seconds to 200 seconds, 5 seconds to 200 seconds, 10 seconds to 200 seconds, 10 seconds to 150 seconds, 10 seconds to 100 seconds, 10 seconds to 80 seconds, 10 seconds to 50 seconds, 10 seconds to 40 seconds, 10 seconds to 30 seconds, 15 seconds to 50 seconds, 15 seconds to 40 seconds, 15 seconds to 30 seconds, or 15 seconds to 25 seconds.

In some embodiments, the cumulative duration of the vibrating mode of operation, or the cumulative duration during which vibration cycles are occurring, is in the range of 1 hour to 12 hours, 2 hours to 10 hours, 2 hours to 8 hours, 2 hours to 6 hours, 2 hours to 4 hours, or 2 hours to 3 hours. It will be appreciated that the cumulative duration of vibration cycles may be dependent on properties of power source 118.

It will be appreciated by persons skilled in the art that the vibration mode of operation may be intermittent, or interrupted, such that vibrating agitator 114 is operative in the vibration mode for a first duration, for example 30 minutes, then does have any vibration cycles for a second duration, for example 1 hour, and then is operative in the vibration mode and has vibration cycles for a third duration, for example two hours. The cumulative duration relates to the sum of all durations during which vibrating agitator 114 was operative in the vibration mode and included vibration cycles, including the vibration duration and the repose duration of the vibration cycle.

In some embodiments, vibrating agitator 114 is configured to exert forces on the capsule housing 112, such that a net force exerted by the capsule housing 112 on the environment thereof is in the range of 50 grams force (gf) to 600 gf, 50 gf to 550 gf, 100 gf to 550 gf, 100 gf to 500 gf, 150 gf to 500 gf, 200 gf to 500 gf, or 200 gf to 450 gf.

In some embodiments, vibrating agitator 114 is configured to exert said forces on capsule housing 112 to attain a capsule housing 112 vibrational frequency within a range of 10 Hz to 650 Hz, 15 Hz to 600 Hz, 20 Hz to 550 Hz, 30 Hz to 550 Hz, 50 Hz to 500 Hz, 70 Hz to 500 Hz, 100 Hz to 500 Hz, 130 Hz to 500 Hz, or 150 Hz to 500 Hz.

It will be appreciated that the exact specifications of the capsule, such as the specific frequency and force ranges applicable to a specific capsule, are dependent on the specifications of the power source 118 and of the vibrating agitator 114.

It will be further appreciated that a specific capsule may be controlled by the control element 116 such that different vibrational frequencies may be attained and/or different net forces may be exerted, by the capsule in different vibration cycles of the capsule. Due to the natural distinction between users, use of multiple different parameters in different vibration cycles of a single capsule would allow the capsule to successfully treat multiple users, even if the personal optimal treatment for those users is not the same, as there is a higher chance that in at least some of the vibration cycles the activation parameters of the capsule would reach, or be close to, the optimal parameters for each specific user.

Control element 116 is adapted to control the operation of intermittently activated vibrating agitator 114. Such control may include control of any one or more of the force applied by the vibrating agitator 114, the vibrational frequency reached, the times in which vibrating agitator 114 operates in the vibration mode of operation, the vibration duration of each vibration cycle, the repose duration of each vibration cycle, the vibration cycle duration, and cumulative vibration duration of the vibrating agitators.

In some embodiments, control element 116 is adapted to receive information relating to the desired vibration protocol from control unit 140, prior to ingestion of device 100 and capsule 110 or to activation of the capsule, or during the device's and capsule's traversal of the user's GI tract. For example, the information may be remotely transmitted from control unit 140 to control element 116, for example using a short range wireless communication method. In some embodiments, the information is transmitted as a list of vibration parameters for effecting the vibration protocol. In some embodiments, the information is transmitted as executable code for effecting the first vibration protocol.

In some embodiments, the information includes a desired number of vibration cycles, a desired vibration duration in each vibration cycle, a desired repose duration in each vibration cycle, a desired cumulative vibration duration, and the like.

In some embodiments, the flowable ingestible medicament is absorbable or at least partially absorbable in the stomach of the user. In some embodiments, the flowable ingestible medicament is absorbable or at least partially absorbable in the small intestine of the user.

In some embodiments, the flowable ingestible medicament has a viscosity in the range of 100 Pa·s to 1000 Pa·s.

In some embodiments, the flowable ingestible medicament is suitable for treatment of one or more symptom or disease, selected from the group consisting of: Parkinsonism; Parkinson's Disease; progressive supranuclear palsy; corticobasal degeneration; multiple system atrophy; Parkinson-plus syndromes (also known as disorders of multiple system degeneration); any neurodegenerative disease in which the subject exhibits at least one (and typically at least two or three) of the classical features of Parkinson's disease: tremor, postural instability, and akinesia or bradykesia; any neurodegenerative disease in which the subject positively responds to a dopaminergic treatment; any neurodegenerative disease in which the particular subject positively responds to an anticholinergic treatment; Constipation; Crohn's disease; Gastroparesis; irritable bowel syndrome (IBS); diarrhea or loose bowel movements; colitis; Hirschsprung's disease; Dyspepsia; and dysphagia.

In some embodiments, the flowable ingestible medicament comprises or includes an ingestible medicament selected from the group consisting of: levodopa; at least one dopaminergic agent; at least one catecholamine precursor; a dopamine precursor; at least one dopamine precursor agent; (L)-3,4-dihydroxyphenylalanine; N-methyl-N-(2-propynyl)-2-methyl-1-phenylethyl-2-amine; tyrosine hydroxylase; apomorphine; at least one anticholinergic agent; at least one agent selected to antagonize at least one cholinergic receptor; benzhexol; orphenadrine; at least one selective allosteric potentiator of metabotropic glutamate receptor 4 (mGluR4); N-phenyl-7-(hydroxylimino)cyclopropa[b]chromen-1a-carboxamide; at least one osmotic agent; magnesium citrate; magnesium hydroxide; polyethylene glycol; sodium phosphate; MiraLAX®; at least one contraction stimulating agent; bisacodyl; senna; Correctol; Ducodyl; Dulcolax; Senexon; Senokot; at least one stool softening agent; docusate sodium; Colace; Linaclotide; Lactulose; lubiprostone; plecanatide; prucaltride; loperamide; and bismuth subsalicylate.

Figure 2:
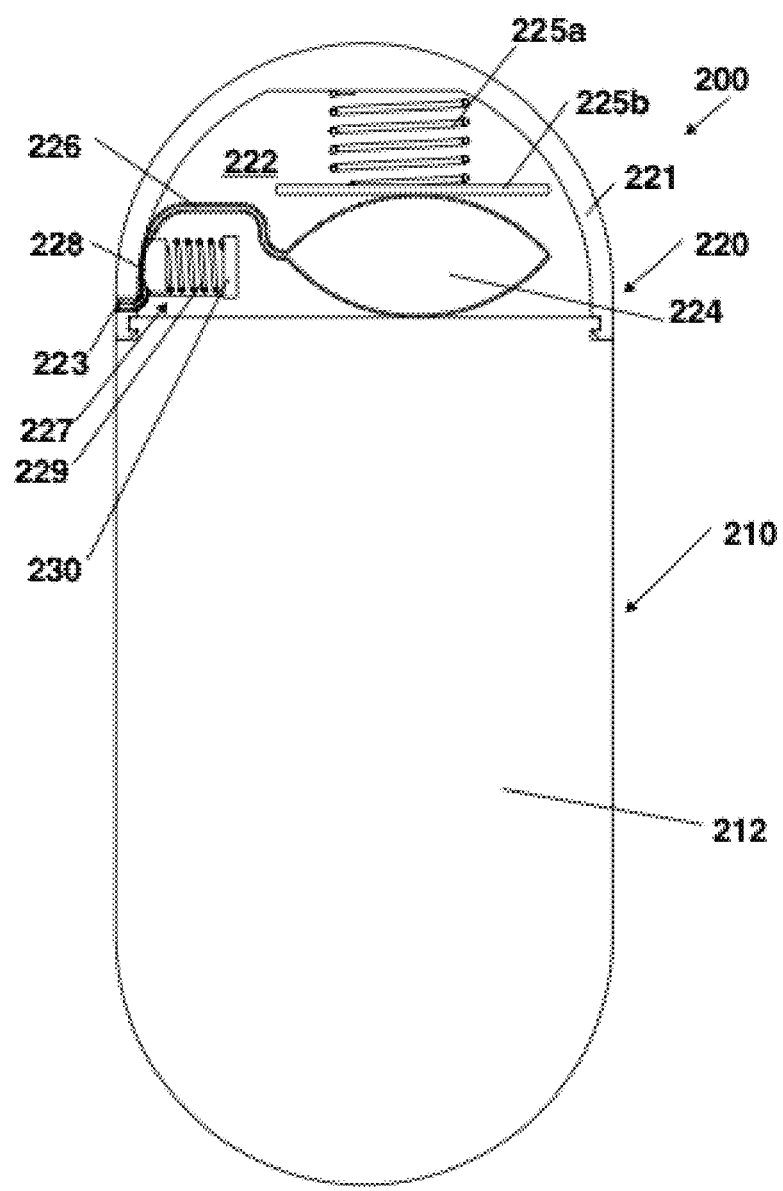
FIG. 2 is a planar sectional illustration of a device for delivering a flowable ingestible medicament into the gastrointestinal tract of a user according to another embodiment of the present invention, the device including a medicament reservoir and a valve.
Figure 3:
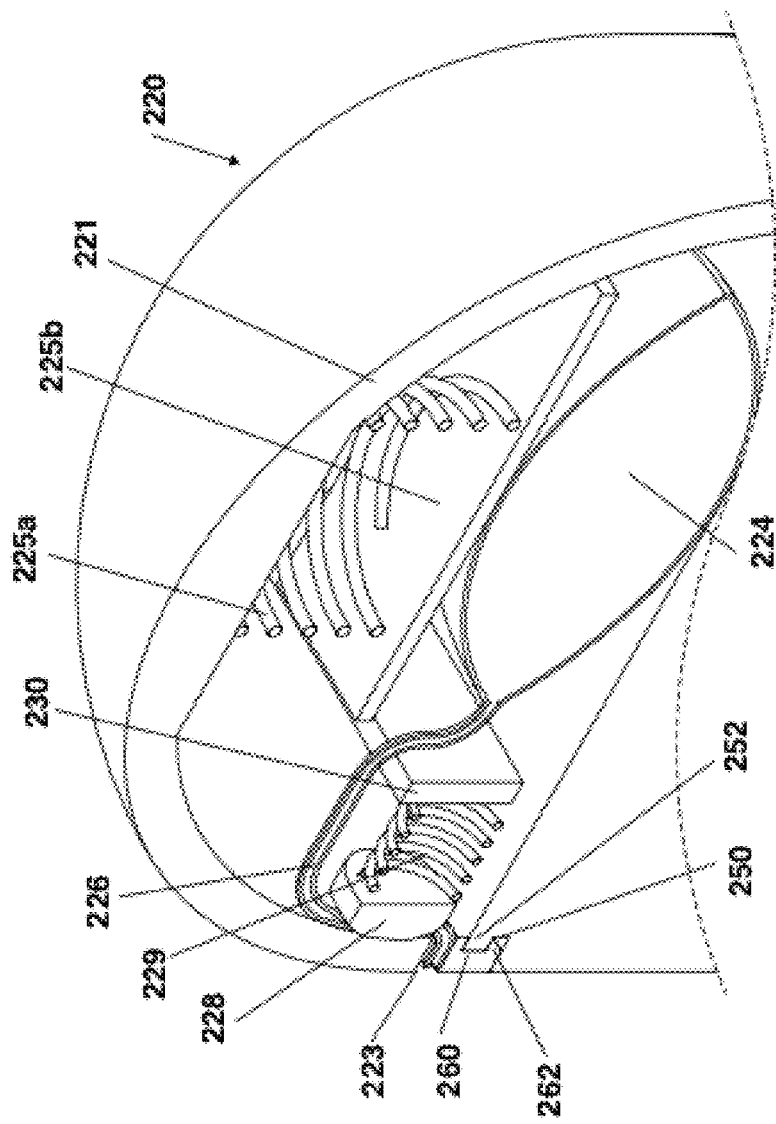
FIG. 3 is a partial perspective sectional illustration of the device of FIG. 2.

Reference is now made to FIG. 2, which is a planar sectional illustration of a device 200 for delivering a flowable ingestible medicament 202 into the gastrointestinal tract of a user according to another embodiment of the present invention, the device including a medicament reservoir 224 and a valve, to FIG. 3, which is a partial perspective sectional illustration of device 200, to FIGS. 4A and 4B, which are partial planar sectional illustrations of device 200, where medicament reservoir 224 is full, and the valve is in closed and open operative orientations, respectively, and to FIG. 5, which is a partial planar sectional illustrations of device 200, where medicament reservoir 124 is empty, and the valve is in a closed operative orientation.

As seen, device 200, which is arranged along a longitudinal axis, includes a vibrating ingestible capsule 210 including a housing 212, substantially as described hereinabove with respect to FIG. 1. It will be appreciated that capsule 210 includes at least a vibrating agitator, a control element, and a power source, as described hereinabove with respect to FIG. 1, even though these components are not explicitly shown in FIGS. 2A to 4B.

A medicament delivery compartment 220, here illustrated as having the shape of a convex dome is formed by a medicament compartment housing 221 which defines a hollow 222. A portal 223 is formed in medicament compartment housing 221. Medicament reservoir 224 is disposed within hollow 222, and is biased toward capsule 210 by a reservoir biasing mechanism. The reservoir biasing mechanism includes a spring 225a anchored at one end thereof to medicament compartment housing 221 and terminating, at an opposing end, in a biasing plate 225b which engages an exterior surface of medicament reservoir 224 and applies pressure thereto. The medicament reservoir 224 is flexible and collapsible, and may be formed of any suitable material such as silicone rubber, natural rubber, polyethylene, and PVC.

A conduit 226, which may be a flexible and/or resilient conduit, extends from medicament reservoir 224 to portal 223, and terminates with portal 223, such that fluid can flow from medicament reservoir 224, via conduit 226 and portal 223, out of the device 200 and into an environment surrounding the device. In some embodiments, the end of conduit 226 disposed within portal 223 also seals the portal, so as to prevent material from the environment entering device 200. In other embodiments, the end of conduit 226 may be surrounded by a seal sealing the portal.

A valve 227 disposed within hollow 222 includes a weight 228 attached to a compression spring 229, which functions as a valve biasing mechanism. The spring 229 is anchored, at an end distal to weight 228, to a rigid anchoring shelf 230 extending from medicament compartment housing 221 or from housing 212 of vibrating ingestible capsule 210.

Biasing spring 229 and weight 228 are constructed such that, when vibrating ingestible capsule 210 is in an inoperative mode, or is in an operative mode but not vibrating, biasing spring 229 biases weight 228 against conduit 226, thus pinching the conduit closed, as illustrated clearly in FIG. 4A. This is the closed operative orientation of valve 227. When valve 227 is in the closed operative orientation, no fluid can flow through conduit 226, and pressure applied by the reservoir biasing mechanism to medicament reservoir 224 is at an equilibrium with forces resisting such pressure by the content of the medicament reservoir and conduit.

However, when vibrating ingestible capsule 210 is in the vibrating mode of operation, vibration of the vibrating ingestible capsule 210 is applied also to biasing spring 229, via anchoring shelf 230. As discussed hereinabove, the vibrations of the capsule 210 are periodic, and cause the spring to periodically contract and extend. Contraction of the spring 229 results in weight 228 being withdrawn, or moved away, from conduit 226, thus enabling the conduit 226 to recover its nominal diameter and fluid to flow through the conduit 226, as illustrated in FIG. 4B. This is the open operative orientation of valve 227. When valve 227 is in the open operative orientation, pressure applied by the reservoir biasing mechanism to medicament reservoir 224 causes medicament 202 to flow from reservoir 224, via conduit 226 and portal 223, into the environment surrounding device 200.

In use, when capsule 210 is in the vibrating mode of operation, valve 227 periodically transitions between the closed operative orientation and the open operative orientation, and vice versa. During such vibration times, and when the valve is in the open operative orientation, flowable ingestible medicament 202 is delivered from reservoir 224 to the environment surrounding device 200. Because of the periodic opening and closing of valve 227, such delivery occurs in bursts, or quanta, until the medicament reservoir is empty and all the flowable medicament has been delivered, as illustrated in FIG. 5.

The volume of medicament delivered in each such burst, is dependent on the pressure applied by the reservoir biasing mechanism, the recovery time of conduit 226, the diameter of the conduit, and the duration that valve 227 is in the open operative orientation. The duration that valve 227 is in the open operative orientation is based on the frequency of vibrations exerted by vibrating ingestible capsule 210, as well as on the mass of weight 228, the length and spring constant of biasing spring 229, and the rigidity of anchoring shelf 230. In some embodiments, the valve 227 functions as a gear reducer, such that the frequency at which the valve transitions between the open and closed configurations is lower than the frequency of vibration of the capsule 210.

Medicament compartment housing 221 of medicament delivery compartment 220 is attached to housing 212 of vibrating ingestible capsule 210. In the illustrated embodiment, housing 212 of vibrating ingestible capsule 210 includes a first attachment mechanism in the form of a circumferential slot 250 and a circumferential protrusion 252 disposed adjacent a longitudinal end 254 of capsule housing 212. Medicament compartment housing 221 includes a second, corresponding attachment mechanism in the form of a circumferential slot 260 and a circumferential protrusion 262 disposed adjacent an end 264 of medicament compartment housing 221. Circumferential slot 260 corresponds in dimensions to circumferential protrusion 252 of capsule 210, and circumferential protrusion 262 corresponds in dimensions to circumferential slot 250 of capsule 210.

In the illustrated embodiment, medicament compartment housing 220 is fixedly attached to vibrating ingestible capsule 210 by snap fit engagement of slot 260 with protrusion 252 and snap fit engagement of protrusion 262 with slot 250. However, any type of attachment between medicament compartment housing 221 and vibrating ingestible capsule 210 is considered within the scope of the present invention, including threaded engagement, engagement by soldering, engagement by adhesive, and the like.

Figure 6:
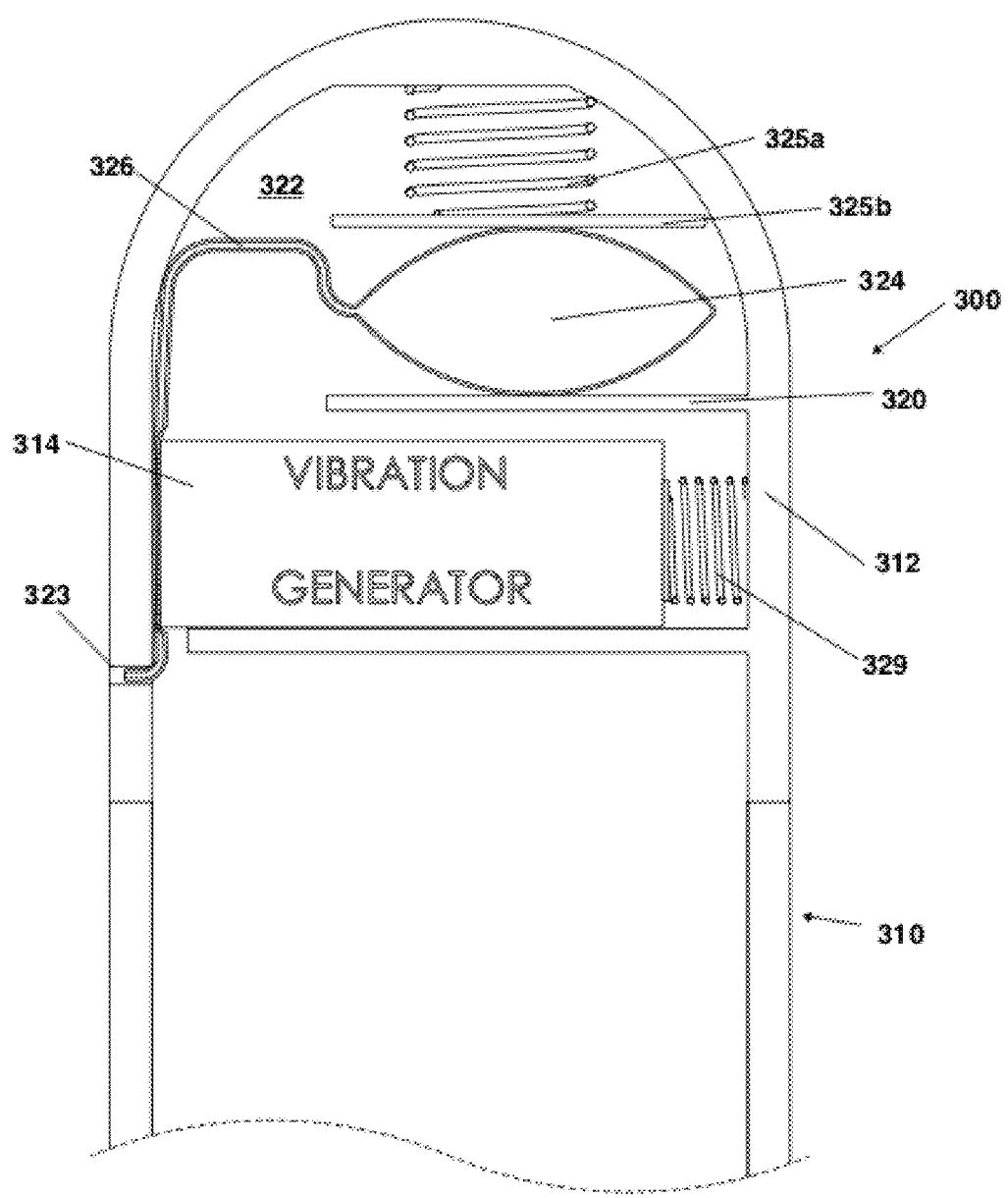
FIG. 6 is a schematic diagram of a device for delivering a flowable ingestible medicament into the gastrointestinal tract of a user according to yet another embodiment of the present invention.

Reference is now made to FIG. 6, which is a schematic diagram of a device 300 for delivering a flowable ingestible medicament 302 into the gastrointestinal tract of a user according to yet another embodiment of the present invention As seen, device 300, which is arranged along a longitudinal axis, includes a vibrating ingestible capsule 310 including a housing 312, formed of a first housing portion and a second housing portion which define a single hollow, and a vibrating agitator 314, substantially as described hereinabove with respect to FIG. 1. It will be appreciated that capsule 310 also includes a control element, and a power source, as described hereinabove with respect to FIG. 1, even though these components are not explicitly shown in FIG. 6.

Vibrating ingestible capsule 310 also functions as a medicament delivery compartment, such that a portal 323 is formed in the second housing portion of housing 312. A medicament reservoir 324 is disposed within a hollow of capsule 310, and is biased toward a shelf 320 extending radially inwardly from housing 312 by a reservoir biasing mechanism. The reservoir biasing mechanism includes a spring 325a anchored at one end thereof to a longitudinal end of housing 312 and terminating, at an opposing end, in a biasing plate 325b which engages an exterior surface of medicament reservoir 324 and applies pressure thereto. The medicament reservoir 324 is flexible and collapsible, and may be formed of any suitable material such as silicone rubber, natural rubber, polyethylene, and PVC.

A conduit 326, which may be a flexible and/or resilient conduit, extends from medicament reservoir 324 to portal 323, and terminates with portal 323, such that fluid can flow from medicament reservoir 324, via conduit 326 and portal 323, out of the device 300 and into an environment surrounding the device. In some embodiments, the end of conduit 326 disposed within portal 323 also seals the portal, so as to prevent material from the environment entering device 300. In other embodiments, the end of conduit 326 may be surrounded by a seal sealing the portal.

Vibrating agitator 314 is attached to a biasing spring 329, which is anchored to housing 312. Vibrating agitator 312 and compression spring 329 form a valve, which functions in the manner described above with respect to valve 227 of FIGS. 2 to 5, which functions as a valve biasing mechanism. The spring 229 is anchored, at an end distal to weight 228, to a rigid anchoring shelf 230 extending from medicament compartment housing 221 or from housing 212 of vibrating ingestible capsule 210.

As such, in a closed operative orientation of the valve, biasing spring 329 biases vibrating agitator 314 against conduit 326, thus pinching the conduit closed. In this closed operative orientation, no fluid can flow through conduit 326, and pressure applied by the reservoir biasing mechanism to medicament reservoir 324 is at an equilibrium with forces resisting such pressure by the content of the medicament reservoir and conduit.

However, when vibrating agitator 314 is in the vibrating mode of operation, biasing spring 329 periodically contracts and extends, resulting in vibrating agitator 314 being periodically withdrawn, or moved away, from conduit 326, thus transitioning the valve to an open operative orientation, enabling conduit 326 to recover its nominal diameter and allowing fluid to flow through conduit 326. When the valve is in the open operative orientation, pressure applied by the reservoir biasing mechanism to medicament reservoir 324 causes medicament 302 to flow from reservoir 324, via conduit 326 and portal 323, into the environment surrounding device 300.

The delivery of the flowable medicament into the environment is as described hereinabove with respect to FIGS. 2 to 5.

Reference is now additionally made to FIG. 7, which is a schematic flowchart of a method for delivering a flowable ingestible medicament into the gastrointestinal tract of user according to the present invention. The method may be based on the use of a device including a vibrating ingestible capsule and a flowable ingestible medicament, as described hereinabove with reference to FIGS. 1 to 6.

As seen at step 400, a device, such as device 100, 200, or 300 described hereinabove, including a vibrating ingestible capsule and a medicament delivery compartment, is provided to a user.

In some embodiments, at step 402, the vibrating ingestible capsule and the medicament delivery compartment are attached to each other. In some embodiments, step 402 may take place in a factory, prior to providing the device to the user at step 400. In other embodiments, the device may be provided to the user as two separate pieces, namely the ingestible vibrating capsule and the medicament delivery compartment, and the user carries out step 402 following receipt of the device at step 400. In some embodiments, in which the device is constructed as a unitary structure, for example as illustrated in FIG. 6, step 402 may be obviated.

In some embodiments, the attaching at step 402 includes fixedly attaching the medicament delivery compartment to the vibrating ingestible capsule.

In some embodiments, the attaching at step 402 includes removably attaching the medicament delivery compartment to the vibrating ingestible capsule.

In some embodiments, the attaching at step 402 includes attaching the medicament delivery compartment to the vibrating ingestible capsule by one or more of snap fit engagement, threaded engagement, adhering, soldering, or any other suitable mechanism of attachment.

In some embodiments, the attaching at step 402 includes mutually attaching a first attachment mechanism on the vibrating ingestible capsule with a corresponding attachment mechanism on the medicament delivery compartment, for example as described with respect to FIGS. 2 to 5.

In some embodiments, the device is provided to the user having the flowable ingestible medicament disposed within the medicament reservoir and within the medicament delivery compartment.

In other embodiments, at step 404, the flowable ingestible medicament is inserted into medicament delivery compartment. Step 404 may include filling of the medicament reservoir with the flowable ingestible medicament and/or inserting the medicament reservoir into the medicament delivery compartment or into the device.

In some embodiments, step 404 takes place prior to attaching the ingestible vibrating capsule with the medicament delivery compartment, either in a factory or by the user. The flowable ingestible medicament inserted at step 404 may be any suitable type of flowable ingestible medicament, as described in detail hereinabove.

Regardless of when the medicament reservoir is inserted into the device, the medicament reservoir is placed under pressure within the device, as explained hereinabove.

At step 406, the device, including the vibrating ingestible capsule, the medicament delivery compartment, and the flowable ingestible medicament, is ingested by the user, and begins to travel through the gastrointestinal tract of the user.

At step 408, which occurs following the user ingesting the device at step 406, the vibrating ingestible capsule is controlled such that the vibration mode of operation (e.g., when the vibration mode is initiated, a duration of the vibration mode, etc.) at least partially transpire within an area of the gastrointestinal tract at which the flowable ingestible medicament should be delivered, or within an absorption time period of the flowable ingestible medicament within the gastrointestinal tract of the user.

The absorption time period may be an estimated absorption time period, as defined herein, and/or an actual absorption time period as defined herein.

In some embodiment, step 408 may include controlling a timing of the vibration mode of operation such that the vibration mode at least partially transpires when the capsule is in a region of the gastrointestinal tract in which the flowable ingestible medicament is typically absorbed into the bloodstream. The region of the gastrointestinal tract may include one or more of the stomach of the user, the duodenum of the user, the small intestine of the user, the large intestine of the user, or the colon of the user.

For example, when the flowable ingestible medicament is levadopa, which is typically absorbed into the bloodstream through the stomach walls and/or the small intestine walls, the vibration mode at least partially transpires within a time period in which the device traverses, or is expected to traverse, the stomach and small intestine.

In some embodiments, step 408 includes setting at least one vibration parameter of the vibrating ingestible capsule of the device so as to promote delivery of flowable ingestible medicament into the gastrointestinal tract of the user or absorption of the ingestible medicament into the bloodstream of the user. In some such embodiments, the at least one vibration parameter set at step 408 includes at least one of a vibration frequency, a cumulative vibration duration, a number of vibration cycles per time unit, a duration of a vibration duration within a vibration cycle, a duration of a repose duration within a vibration cycle, a total duration of a single vibration cycle, and a net force exerted by said housing on said environment.

In some embodiments, the controlling at step 408 includes controlling the vibrating agitator such that the vibrating mode of operation includes a plurality of cycles, each of the cycles including a vibration duration followed by a repose duration, wherein the housing exerts the vibrations during the vibration duration.

In some embodiments, the repose duration is greater than the vibration duration.

In some embodiments, the vibration duration is in the range of 0.1 second to 10 seconds, 1 second to 10 seconds, 1 second to 9 seconds, 2 seconds to 9 seconds, 3 seconds to 9 seconds, 3 seconds to 8 seconds, 3 seconds to 7 seconds, 3 seconds to 6 seconds, 4 seconds to 6 seconds, or 5 seconds to 6 seconds.

In some embodiments, the repose duration is in the range of 1 second to 180 seconds, 3 seconds to 180 seconds, 5 seconds to 180 seconds, 5 seconds to 150 seconds, 5 seconds to 120 seconds, 8 seconds to 100 seconds, 8 seconds to 30 seconds, 10 seconds to 80 seconds, 10 seconds to 70 seconds, 10 seconds to 60 seconds, 10 seconds to 50 seconds, 10 seconds to 40 seconds, 10 seconds to 30 seconds, 10 seconds to 20 seconds, or 15 seconds to 20 seconds.

In some embodiments, a duration of each of the plurality of cycles is in the range of 1.1 seconds to 200 seconds, 5 seconds to 200 seconds, 10 seconds to 200 seconds, 10 seconds to 150 seconds, 10 seconds to 100 seconds, 10 seconds to 80 seconds, 10 seconds to 50 seconds, 10 seconds to 40 seconds, 10 seconds to 30 seconds, 15 seconds to 50 seconds, 15 seconds to 40 seconds, 15 seconds to 30 seconds, or 15 seconds to 25 seconds.

In some embodiments, the controlling at step 408 includes controlling the vibrating agitator such that a cumulative duration of the vibrating mode of operation is in the range of 1 hour to 12 hours, 2 hours to 10 hours, 2 hours to 8 hours, 2 hours to 6 hours, 2 hours to 4 hours, or 2 hours to 3 hours.

In some embodiments, the controlling at step 408 includes controlling the vibrating agitator to exert forces on the housing of the vibrating ingestible capsule, such that a net force exerted by the housing on the environment thereof is in the range of 50 grams force (gf) to 600 gf, 50 gf to 550 gf, 100 gf to 550 gf, 100 gf to 500 gf, 150 gf to 500 gf, 200 gf to 500 gf, or 200 gf to 450 gf.

In some embodiments, the controlling at step 408 includes controlling the vibrating agitator to exert the forces on the housing to attain a housing vibrational frequency within a range of 10 Hz to 650 Hz, 15 Hz to 600 Hz, 20 Hz to 550 Hz, 30 Hz to 550 Hz, 50 Hz to 500 Hz, 70 Hz to 500 Hz, 100 Hz to 500 Hz, 130 Hz to 500 Hz, or 150 Hz to 500 Hz.

In some embodiments, and as described in further detail herein, the method may include a further step 412 of transitioning the capsule (from an inoperative state) to an operative state.

The capsule may be pre-programmed with a vibration protocol. This protocol may include, by way of example, a particular or pre-determined activation time following ingestion, in which the capsule is transitioned from an inoperative state to an operative state. In such embodiments, the step 412 may be omitted from the method.

Alternatively or additionally, the capsule may receive an activation input in an active fashion (e.g., from an external controller via RF) or in a passive fashion (e.g., a signal from a sensor to the on-board controller), as described in detail hereinabove. It will be appreciated that step 412, in which the vibrating ingestible capsule is transitioned from the inoperative state to the operative state, may be performed prior to ingestion of the device by the user in step 406, or following such ingestion, for example in the case of external control via RF.

Substantially as described hereinabove, step 412 may be carried out, and the vibrating ingestible capsule may be activated, prior to the user ingesting the capsule at step 406, for example by a signal from the control unit or by the user carrying out an activation motion. In other embodiments, the activation input, and the transitioning of the capsule from being inoperative to being operative, occurs at the time of ingestion or immediately thereafter, for example by sensors sensing a change in the environment of the capsule due to its ingestion, as described at length hereinabove. In yet other embodiments, the transitioning of the capsule at step 412 may include the capsule receiving an activation input which is provided remotely when the capsule is already in the body of the user, for example by remote communication from control module 140. In some embodiments, a control element of the vibrating ingestible capsule may optionally receive a desired vibration protocol for the user, at an optional step 414. In some embodiments, the programming of the desired vibration protocol at step 414 occurs at the time of manufacturing of the vibrating ingestible capsule or of the device, for example by pre-programming the protocol into the control element. In other embodiments, providing the desired vibration protocol for the user at step 414 may be effected by a control unit, such as control unit 140 of FIG. 1, as described in detail hereinabove with respect to FIG. 1.

In some embodiments, following expelling of the capsule from the subject's body, the capsule may be detected by a toilet bowl mounted sensor, thereby to confirm that the capsule has been expelled from the subject's body.

It will be appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable sub-combination.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims. All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention.

What is claimed is:

1. A medicament delivery compartment, adapted to be attached to a vibrating ingestible capsule having a first housing portion and adapted to operate in a vibrating mode of operation, for delivery of a flowable ingestible medicament into the gastrointestinal tract of a user, the medicament delivery compartment including:
    a second housing portion adapted to be attached to said first housing portion of said vibrating ingestible capsule, and having a portal formed therein;
    a flexible and collapsible medicament reservoir dimensioned to contain the flowable ingestible medicament;
    a reservoir biasing mechanism adapted to apply pressure to said flexible and collapsible medicament reservoir;
    a resilient conduit extending from said medicament reservoir to said portal, and sealing said portal; and
    a valve including a weight and a valve biasing mechanism adapted, in a closed operative orientation, to bias said weight against said conduit so as to pinch said conduit and to block flow through said conduit, and in an open operative orientation to remove the weight from said conduit so as to allow said conduit to recover and fluid to flow through said conduit,
    wherein said valve is adapted to be functionally associated with said first housing portion, such that when the vibrating ingestible capsule is in the vibrating mode of operation, vibrations exerted on the first housing portion are applied to said valve biasing mechanism and are adapted to periodically transition said valve between said closed operative orientation and said open operative orientation.

2. The medicament delivery compartment of claim 1, wherein said valve is configured to be in said open operative orientation and to enable flow through said conduit when the vibrating ingestible capsule is in the vibration mode of operation.

3. The medicament delivery compartment of claim 1, wherein at least one valve parameter of said valve is set such that said valve opens and closes at a frequency smaller than a frequency of vibration of the vibrating ingestible capsule.

4. Medicament delivery compartment of claim 3, wherein said at least one valve parameter includes at least one of a mass of said weight, a length of said valve biasing mechanism, and a spring constant of said valve biasing mechanism.

5. The medicament delivery compartment of claim 1, wherein said second housing portion comprises an attachment mechanism for mutual attachment to a corresponding attachment mechanism of the first housing portion of the vibrating ingestible capsule.

6. The medicament delivery compartment of claim 1, wherein a hollow formed in said second housing portion has a volume in the range of 200 $mm^3$ to 3000 $mm^3$.

7. The medicament delivery compartment of claim 1, wherein said flexible and collapsible medicament reservoir has a Young's modulus smaller than 1 GPa.

8. The medicament delivery compartment of claim 1, wherein said reservoir biasing mechanism comprises a reservoir spring terminating in a pressure applying surface, the pressure applying surface engaging an exterior surface of said medicament reservoir, said reservoir spring is anchored to said second housing portion.

9. The medicament delivery compartment of claim 1, wherein a recovery time of said conduit is at most equal to one or more of:
    0.1 seconds;
    1/f, where f is a frequency of said vibrating agitator; and
    1/fv, where fv is a frequency of said valve biasing mechanism moving from said open operative orientation to said closed operative orientation and back to said open operative orientation.

10. The medicament delivery compartment of claim 1, wherein said conduit has a diameter in the range of 0.01 mm to 0.9 mm.

11. The medicament delivery compartment of claim 1, wherein said valve biasing mechanism is adapted to be anchored to the vibrating ingestible capsule.

12. The medicament delivery compartment of claim 1, wherein said valve biasing mechanism is adapted to be anchored to said second housing portion.

13. The medicament delivery compartment of claim 1, further comprising said flowable ingestible medicament disposed within the medicament reservoir.

14. The medicament delivery compartment of claim 13, wherein said flowable ingestible medicament has a viscosity in the range of 100 Pa·s to 1000 Pa·s.

15. The medicament delivery compartment of claim 1, wherein said valve is transitioned between said closed operative orientation and said open operative orientation solely during the vibrating mode of operation of the vibrating ingestible capsule.

16. The medicament delivery compartment of claim 1, wherein said flexible and collapsible medicament reservoir has a maximal volume in the range of 0.5 ml to 15 ml.

17. The medicament delivery compartment of claim 1, wherein said conduit has a length in the range of 3 mm to 25 mm.

18. The medicament delivery compartment of claim 1, wherein said conduit is flexible.

19. A method for delivering an ingestible medicament into a gastrointestinal tract of a user, the method comprising:
attaching the medicament delivery compartment according to claim 13 to a vibrating ingestible capsule to form a medicament delivery device;
providing to the user said medicament delivery device for ingestion by the user; and
following the user ingesting said medicament delivery device, controlling operation of said vibrating ingestible capsule such that said vibration mode of operation at least partially transpires within a region of the gastrointestinal tract in which the flowable ingestible medicament is absorbable by the user, thereby to cause periodic transitioning of said valve between said closed operative orientation and said open operative orientation, and delivery of said flowable ingestible medicament from said reservoir, via said conduit and said portal, into the environment surrounding said medicament delivery device.

20. A method for delivering an ingestible medicament into a gastrointestinal tract of a user, the method comprising:
filling the medicament delivery compartment according to claim 1 with said flowable ingestible medicament;
attaching the filled medicament delivery compartment to a vibrating ingestible capsule to form a medicament delivery device;
providing to the user said medicament delivery device for ingestion by the user; and
following the user ingesting said medicament delivery device, controlling operation of said vibrating ingestible capsule such that said vibration mode of operation at least partially transpires within a region of the gastrointestinal tract in which the flowable ingestible medicament is absorbable by the user, thereby to cause periodic transitioning of said valve between said closed operative orientation and said open operative orientation, and delivery of said flowable ingestible medicament from said reservoir, via said conduit and said portal, into the environment surrounding said medicament delivery device.

* * * * *